(12) United States Patent  
Iwahori et al.

(10) Patent No.: US 9,144,476 B2  
(45) Date of Patent: Sep. 29, 2015

(54) ELECTRIC TOOTHBRUSH

(75) Inventors: Toshiyuki Iwahori, Mishima-gun (JP); Akitoshi Miki, Ibaraki (JP)

(73) Assignee: OMRON HEALTHCARE CO., LTD., Kyoto (JP)

(*) Notice: Subject to any disclaimer, the term of this patent is extended or adjusted under 35 U.S.C. 154(b) by 482 days.

(21) Appl. No.: 12/921,506

(22) PCT Filed: Mar. 9, 2009

(86) PCT No.: PCT/JP2009/054422  
§ 371 (c)(1), (2), (4) Date: Sep. 8, 2010

(87) PCT Pub. No.: WO2009/113491  
PCT Pub. Date: Sep. 17, 2009

(65) Prior Publication Data  
US 2011/0010875 A1 Jan. 20, 2011

(30) Foreign Application Priority Data

Mar. 14, 2008 (JP) .............................. 2008-065761  
Nov. 13, 2008 (JP) .............................. 2008-291171

(51) Int. Cl.  
A46B 13/02 (2006.01)  
A61C 17/22 (2006.01)  
A61C 17/32 (2006.01)  
A61C 17/34 (2006.01)  
A46B 15/00 (2006.01)

(52) U.S. Cl.  
CPC .............. *A61C 17/221* (2013.01); *A46B 13/02* (2013.01); *A46B 13/023* (2013.01); *A46B 15/0006* (2013.01); *A61C 17/22* (2013.01)

(58) Field of Classification Search  
CPC ................................ A46B 13/02; A61C 17/22  
USPC .......................................................... 15/22.1  
IPC ......................................................... A46B 13/02  
See application file for complete search history.

(56) References Cited

U.S. PATENT DOCUMENTS 6,536,068 B1 * 3/2003 Yang et al. ...................... 15/105  
7,464,430 B2 * 12/2008 Filsouf ........................... 15/22.1  
(Continued)

FOREIGN PATENT DOCUMENTS

FR 2659848 A1 9/1991  
JP A-52-088442 7/1977  
(Continued)

OTHER PUBLICATIONS

JP 08010045 English Translation.*  
(Continued)

*Primary Examiner* — Monica Carter  
*Assistant Examiner* — Stephanie Berry  
(74) *Attorney, Agent, or Firm* — Oliff PLC

(57) ABSTRACT

A three-axis acceleration sensor is mounted to a body of an electric toothbrush. A CPU detects the three-dimensional attitude of the body based on an output from the acceleration sensor and, based on the attitude of the toothbrush, estimates which portion is being brushed. Then, the CPU performs control for switching between operation modes (such as the rotational direction of a motor and the frequency of vibration of the brush) according to the estimated portion being brushed.

6 Claims, 31 Drawing Sheets

(56) References Cited

U.S. PATENT DOCUMENTS

| | | |
|---|---|---|
| 2002/0183959 A1 | 12/2002 | Savill et al. |
| 2008/0060148 A1 | 3/2008 | Pinyayev et al. |
| 2009/0092955 A1* | 4/2009 | Hwang .................... 434/263 |

FOREIGN PATENT DOCUMENTS

| | | | | |
|---|---|---|---|---|
| JP | U-04-015426 | | 2/1992 | |
| JP | A-05-123221 | | 5/1993 | |
| JP | 08010045 A | * | 1/1996 | ............. A46B 13/02 |
| JP | A-08-010045 | | 1/1996 | |
| JP | A-2005-152217 | | 6/2005 | |
| WO | WO 2006/137648 A1 | | 12/2006 | |
| WO | WO 2007/077512 A2 | | 7/2007 | |

OTHER PUBLICATIONS

Sep. 15, 2011 Office Action issued in Russian Patent Application No. 2010142036/14(060363) (with translation).

International Search Report in International Application No. PCT/JP2009/054422; dated Apr. 14, 2009 (with English-language translation).

May 6, 2014 Office Action issued in Mexican Patent Application No. MX/a/2010/009399 (with translation).

* cited by examiner

FIG.14
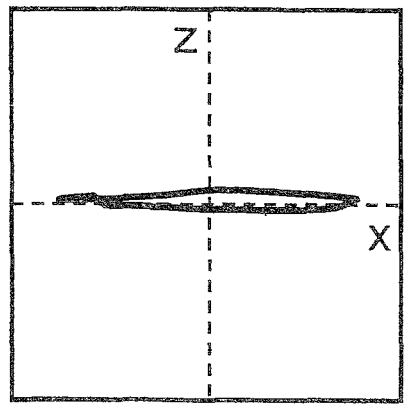
FIRST RESONANCE: ABOUT 12500 spm
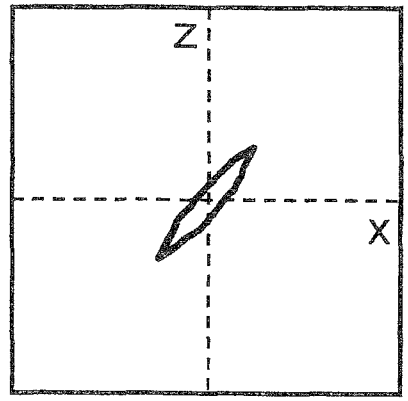
OUT OF RESONANCE: ABOUT 26500 spm
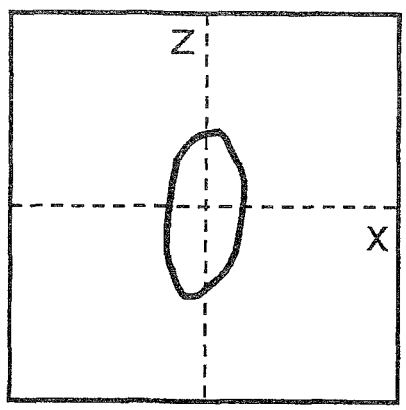
SECOND RESONANCE: ABOUT 38000 spm FIG.29
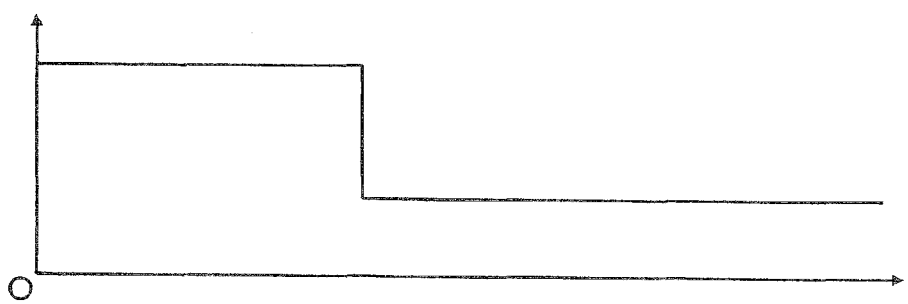
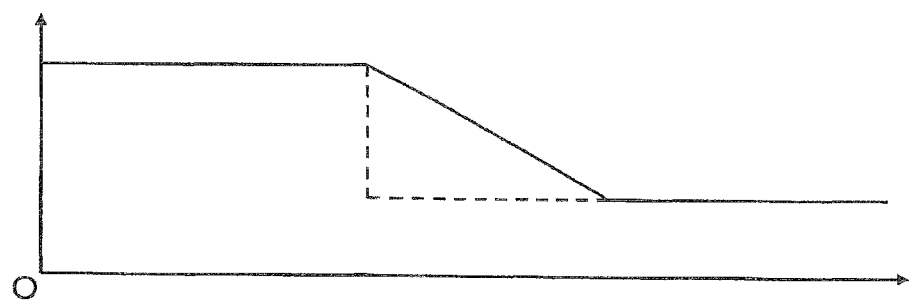

FIG.31
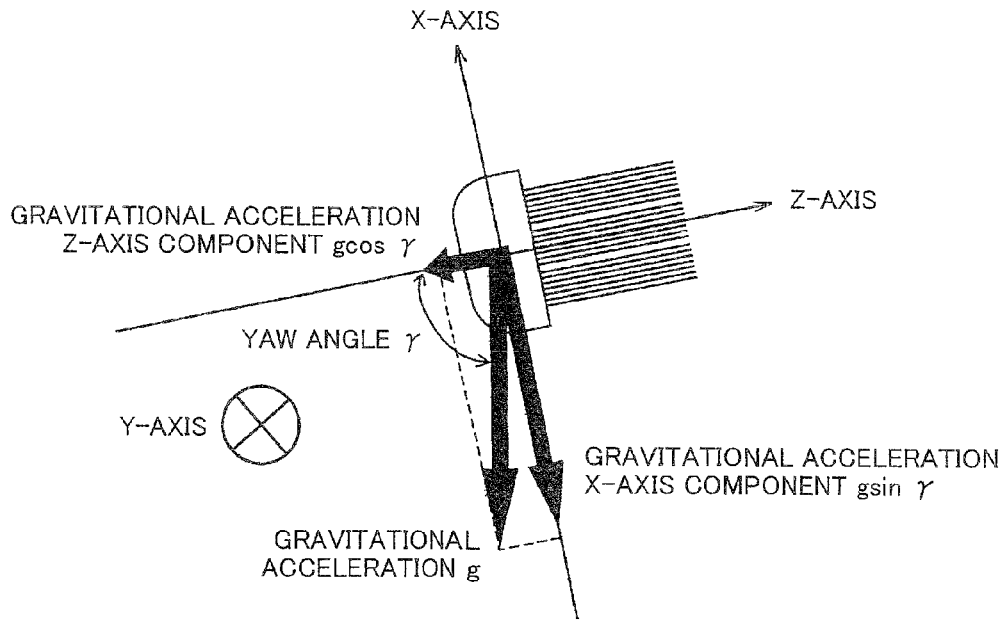
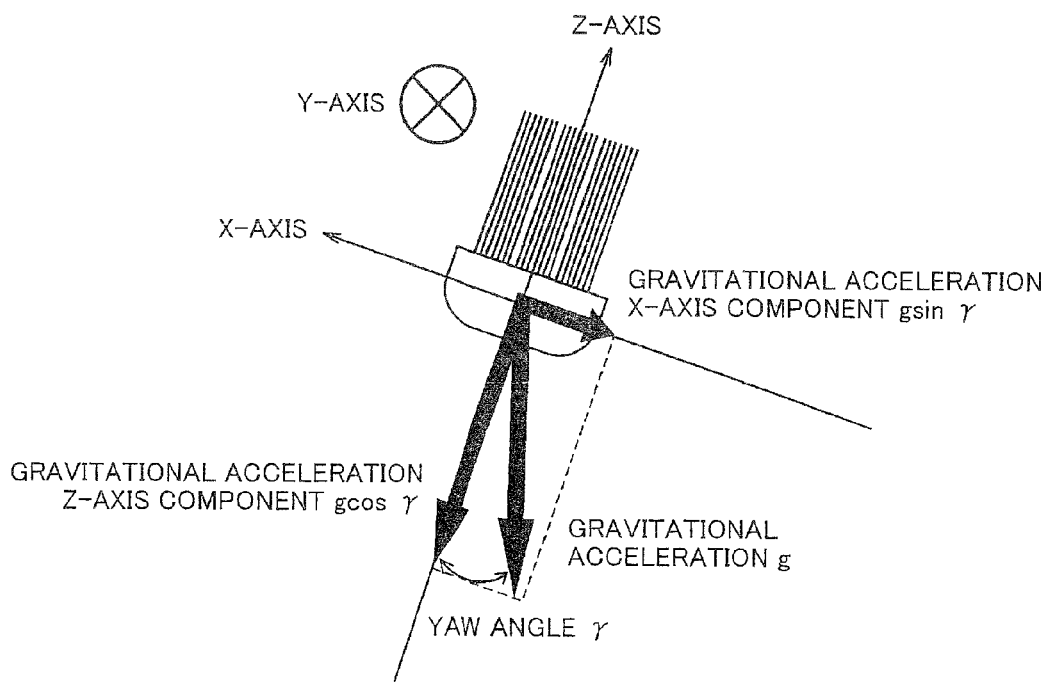

ELECTRIC TOOTHBRUSH

TECHNICAL FIELD

The present invention relates to an electric toothbrush.

BACKGROUND ART

There is known an electric toothbrush of a type which performs toothbrushing (removing food debris and plaque) by placing a fast-moving brush against teeth. For the electric toothbrush of this type, a variety of driving mechanisms and driving methods are proposed with the aim of improving plaque removing power and improving sense of medical treatment.

For example, Patent Documents 1, 2 disclose an electric toothbrush capable of switching between a rotational reciprocating motion (rolling motion) and a linear reciprocating motion by switching rotational directions of a motor.

Furthermore, Patent Document 3 discloses an idea that the orientation around the shaft of the toothbrush body is detected at four stages or eight stages and a section being brushed is estimated based on the detection result. Specifically, a plurality of segments each in the shape of a sector are provided in the circumferential direction in the inside of the body. The orientation of the toothbrush body is estimated by sensing in which segment a conductive ball is present, based on a change of electric resistance. However, it is difficult to reduce the size of such a mechanism, and in addition, it is difficult to obtain high sensing accuracy because the position of the ball is not stable due to motion of the toothbrush. In Patent Document 3, the number of times or time of brushing is recorded for each section, and evaluation as to whether brushing is properly done or not is output.

Patent Document 1: Japanese Utility Model Laying-Open No. 4-15426
Patent Document 2: Japanese Patent Laying-Open No. 5-123221
Patent Document 3: Japanese Patent Laying-Open No. 2005-152217

DISCLOSURE OF THE INVENTION

Problems to be Solved by the Invention

An object of the present invention is to provide a technique for further improving plaque removing power and sense of medical treatment of an electric toothbrush.

Means for Solving the Problems

In order to achieve the above-noted object, the present invention employs the following configuration.

An electric toothbrush in accordance with the present invention includes: a brush; driving means for making the brush into motion; orientation detection means for detecting an orientation of the brush; section estimation means for estimating a section being brushed based on the detected orientation; and control means for switching operation mode of the driving means according to the estimated section being brushed.

Here, the "section being brushed" is a section that is brushed by the brush (touched by the brush) among a plurality of sections defined by segmenting dentition surfaces in the oral cavity. Food debris and plaque adhere in different ways depending on the kinds (maxilla/mandible, molar/incisor, etc.) and portions (tongue-side/cheek-side, tooth surface/occlusal surface, periodontal pocket) of teeth. Therefore, effective brushing operations, for example, such as how to apply the brush, how to move the brush, and speed, are different for each section. Furthermore, even when the kind of teeth is the same, the brush is applied in opposite directions between left and right dentitions.

The electric toothbrush in the present invention therefore employs a configuration in which a section being brushed is automatically estimated and in addition operation mode is automatically switched depending on the estimated section being brushed. Accordingly, a proper brushing operation for each section being brushed can be realized, and further improvement in plaque removing power and sense of medical treatment can be expected.

Preferably, the driving means includes a rotation motor, and the control means switches a rotational direction of the rotation motor according to a section being brushed.

Accordingly, a motion direction of the brush (movement of bristles of the brush) can be changed according to a section being brushed. For example, control can be performed such that the bristles of the brush are moved in a direction in which plaque is scraped off from periodontal pockets.

Preferably, the control means switches a motion frequency of the brush according to a section being brushed.

For example, control can be performed such that the motion frequency is decreased at a sensitive section (a section where strong brushing is not preferable) and the motion frequency is increased at a section where a high brushing effect is desired.

Preferably, the orientation detection means has an acceleration sensor for detecting a three-dimensional orientation of the brush based on output of the acceleration sensor.

Accordingly, the orientation of the brush can be determined with high precision so that a section being brushed can be identified with higher precision and higher resolution than the conventional. In addition, the acceleration sensor, which is compact, can be incorporated easily into the electric toothbrush body. A single-axis acceleration sensor may be used, or a multi-axis (two-axis, three-axis, or more) acceleration sensor may preferably be used.

Preferably, the orientation detection means has a gyroscope for detecting a three-dimensional orientation of the brush based on output of the acceleration sensor and output of the gyroscope.

The output of the acceleration sensor includes a gravitational acceleration component and a dynamic acceleration component. Of these, it is the gravitational acceleration component that indicates the three-dimensional orientation of the brush and the dynamic acceleration component is an unnecessary signal component. Therefore, the three-dimensional orientation of the brush can be calculated with higher precision by referring to output of the gyroscope and cancelling the dynamic acceleration component.

Preferably, the electric toothbrush further includes brush angle estimation means for estimating a brush angle that is an angle of the brush with respect to a tooth axis, based on the detected orientation, and the control means switches operation mode of the driving means according to the estimated section being brushed and brush angle.

A more proper bushing operation can be realized by additionally taking the brush angle into consideration.

Preferably, the electric toothbrush further includes load sensing means for sensing a load acting on the brush, and the control means prohibits switching of the operation mode while no load is acting on the brush.

For example, when the brush is moved from the right-side to the left-side of dentition, the orientation of the brush greatly changes, so that operation mode may be switched frequently during moving. Such a phenomenon is not preferable since it makes control unstable and results in wasted power consumption. Therefore, as in the present invention, the above-noted phenomenon during brush moving can be prevented by prohibiting operation mode switching while no load is acting on the brush.

The present invention can be configured with any possible combination of the means and processes as mentioned above.

Effects of the Invention

The present invention provides further improvement in plaque removing power and sense of medical treatment of an electric toothbrush.

BRIEF DESCRIPTION OF THE DRAWINGS

FIG. 14 is a diagram illustrating a trajectory of a brush.
FIG. 29 is a diagram illustrating driving speed change control.
FIG. 31 is a diagram illustrating orientation detection in an eighth embodiment.

BEST MODES FOR CARRYING OUT THE INVENTION

In the following, suitable embodiments of the present invention will be described in detail with reference to the figures by way of illustration.

First Embodiment

Figure 1:
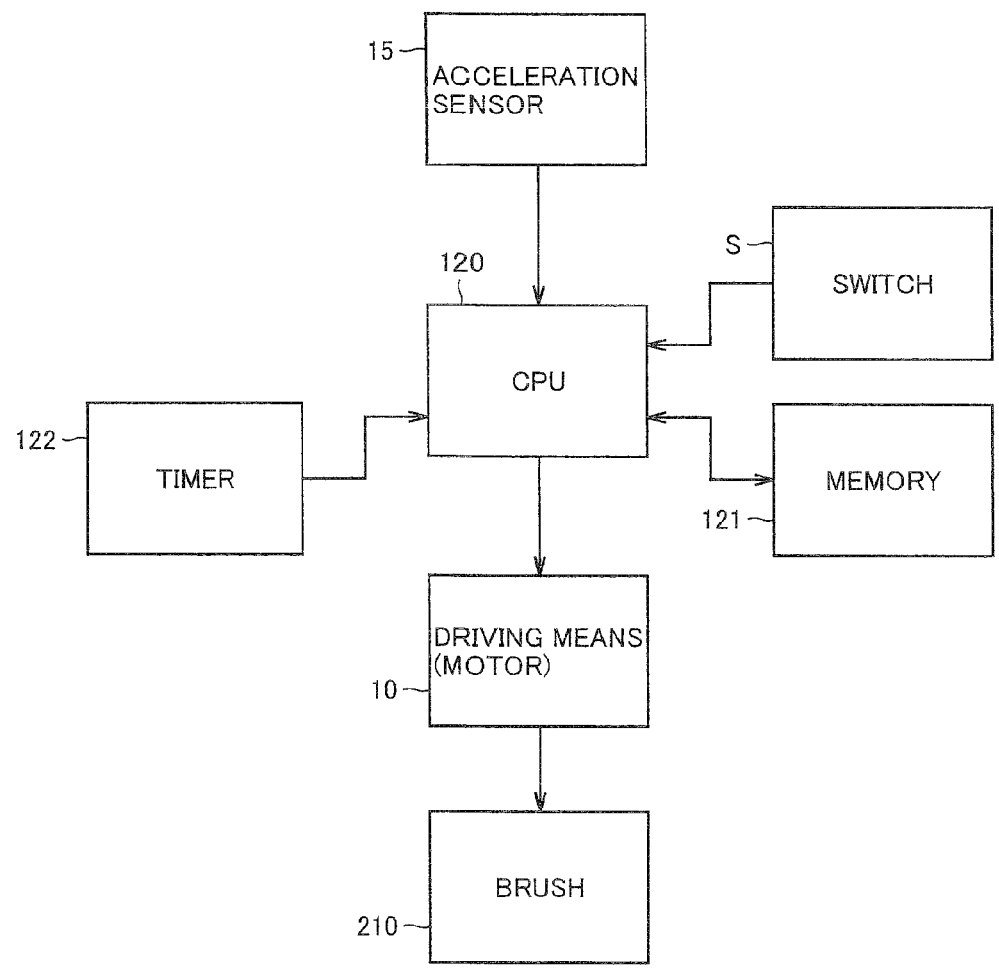
FIG. 1 is a block diagram of an electric toothbrush in a first embodiment.
Figure 2:
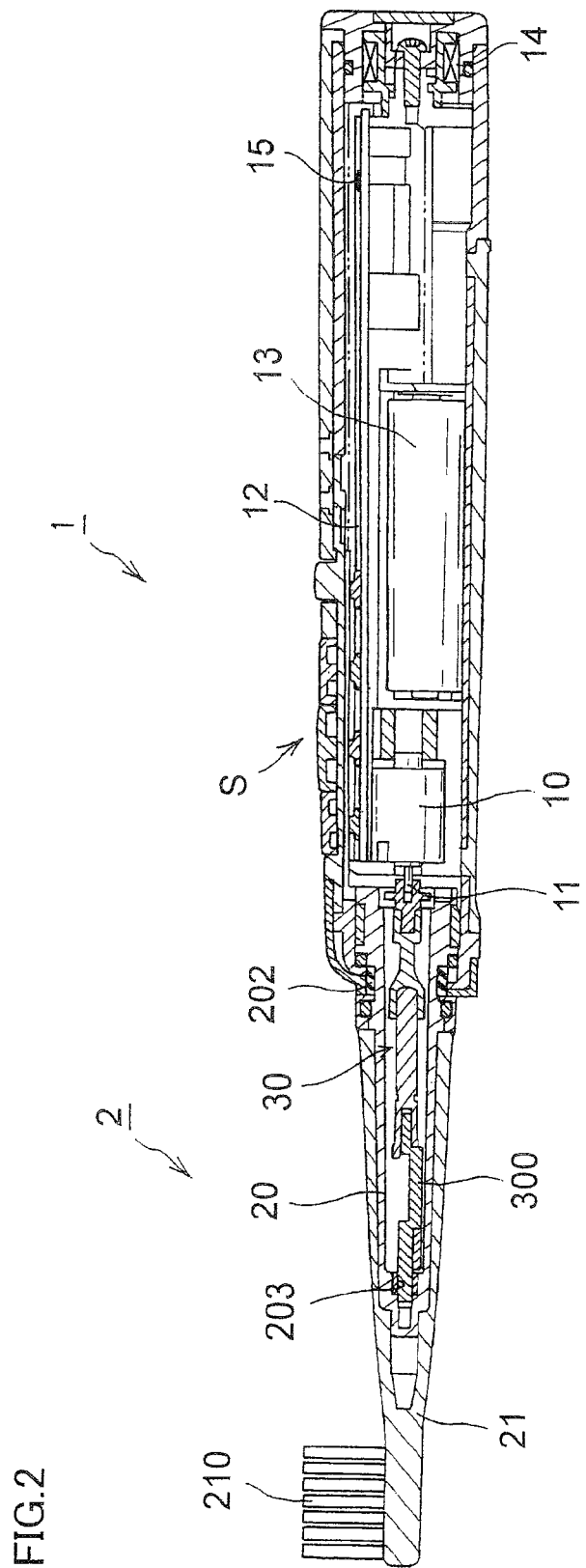
FIG. 2 is a cross-sectional view showing an internal structure of the electric toothbrush in the first embodiment.
Figure 3:
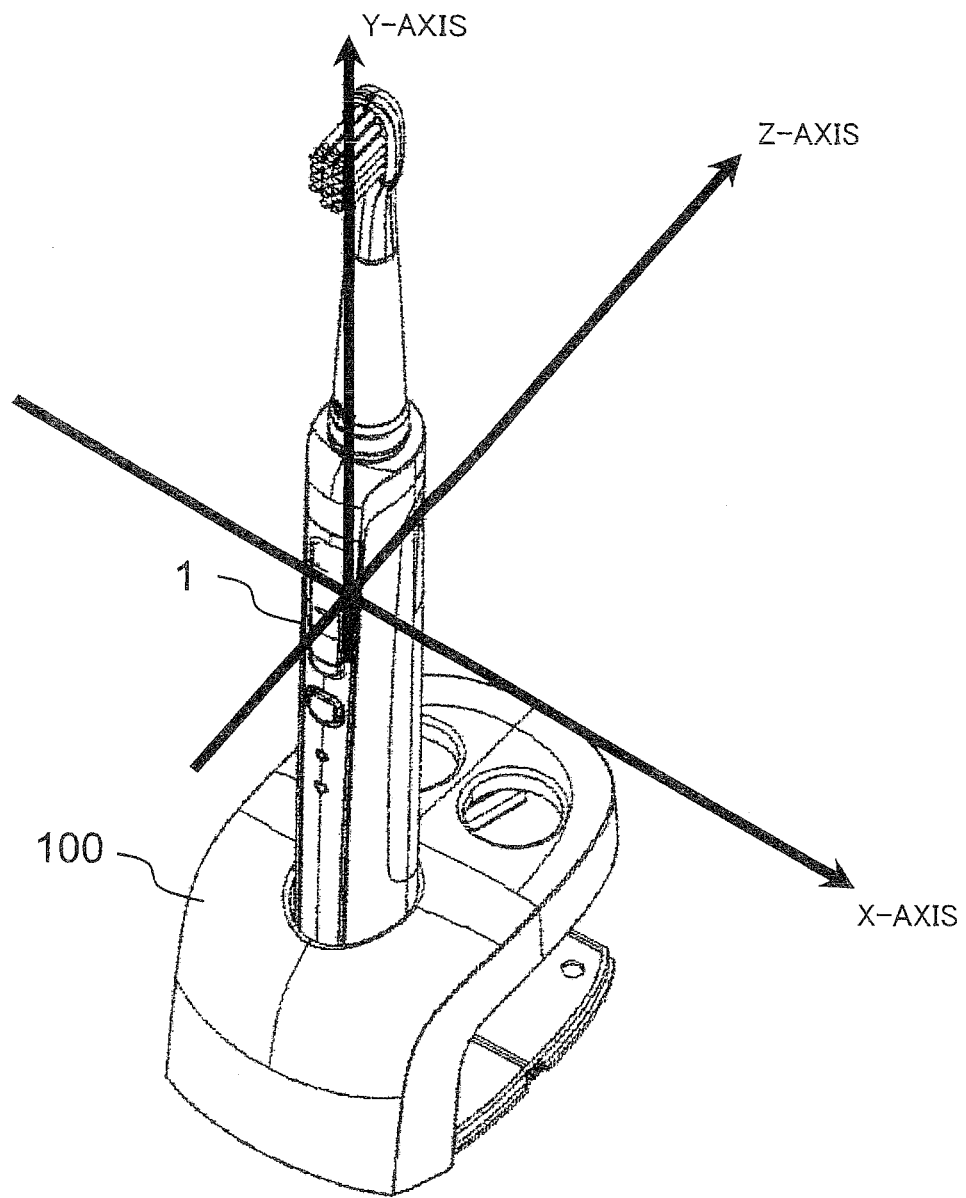
FIG. 3 is a perspective view showing an external view of the electric toothbrush.

<Structure of Electric Toothbrush>
Referring to FIG. 1, FIG. 2, and FIG. 3, a structure of an electric toothbrush will be described. FIG. 1 is a block diagram of an electric toothbrush in a first embodiment, FIG. 2 is a cross-sectional view showing an internal structure of the electric toothbrush in the first embodiment, and FIG. 3 is a perspective view showing an external view of the electric toothbrush.

The electric toothbrush includes an electric toothbrush body 1 (hereinafter simply referred to as "body 1") containing a motor 10 serving as a driving source, and a vibrating member 2 having a brush 210. Body 1 has a generally cylindrical shape and also serves as a handle portion for the user to grip by hand in brushing his/her teeth.

Body 1 is provided with a switch S for turning on/off the power. Provided in the inside of body 1 are motor 10 serving as a driving source, a driving circuit 12, a rechargeable battery 13 serving as a power supply of 2.4 V, a coil 14 for charging, and the like. In order to charge rechargeable battery 13, body 1 is simply placed on a charger 100 so that non-contact charging is realized by electromagnetic induction. Driving circuit 12 has a CPU (input/output processing unit) 120 for executing a variety of operations and control, a memory 121 for storing programs and a variety of setting values, a timer 122, and the like.

A multi-axis (here, three axes of x, y, z) acceleration sensor 15 is further provided in the inside of body 1. As shown in FIG. 3, acceleration sensor 15 is provided such that the x-axis is parallel to the brush face, that the y-axis coincides with the longitudinal direction of body 1, and that the z-axis is vertical to the brush face. In other words, when body 1 is placed on charger 100, the gravitational acceleration vector is parallel to the y-axis. When the brush face is turned up, the gravitational acceleration vector is parallel to the z-axis. When the brush face is turned sideways with body 1 oriented horizontally, the gravitational acceleration vector is parallel to the x-axis. Output of each axis of acceleration sensor 15 is input to CPU 120 for use to detect the three-dimensional orientation of the brush.

Figure 27:
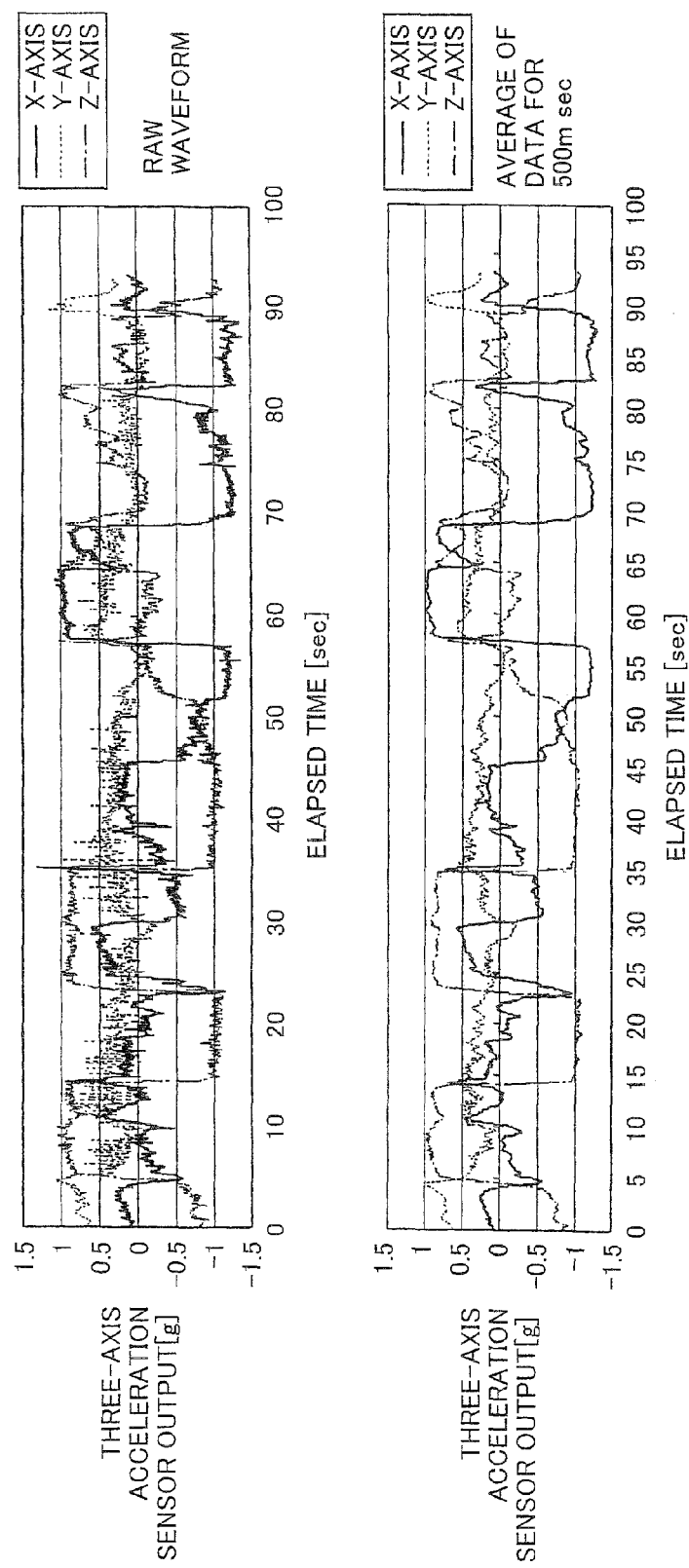
FIG. 27 is a diagram illustrating noise reduction of acceleration sensor output.

A piezo resistance-type, capacitance-type, or heat sensing-type MEMS sensor may preferably be used as acceleration sensor 15. This is because an MEMS sensor is very small and is easily incorporated in the inside of body 1. However, the type of acceleration sensor 15 is not limited thereto and an electrodynamic-type, strain gauge-type, piezoelectric-type sensor may be used. Although not particularly shown in the figures, a correction circuit may be provided for correcting balance of sensor sensitivity between axes, temperature characteristics of sensitivity, temperature drift, etc. In addition, a bandpass filter (lowpass filter) may be provided for removing dynamic acceleration components or noise. Furthermore, noise may be reduced by smoothing the output waveform of the acceleration sensor. FIG. 27 shows an example in which high-frequency noise of output waveform is reduced by averaging data of around a few tens of msec.

Vibrating member 2 includes a stem portion 20 fixed to the body 1 side and a brush part 21 attached to this stem portion 20. A brush 210 is embedded in the tip end of brush part 21. Brush part 21 is a consumable and is thus configured to be removable from stem portion 20 so that it can be replaced with a new one.

Stem portion 20 is made of a resin material. Stem portion 20 is mounted on body 1 with an elastic member 202 of elastomer interposed. Stem portion 20 is a tubular member which is closed at the tip end (the brush-side end) and has a bearing 203 at the tip end in the inside of the tube. A tip end of an eccentric shaft 30 coupled to a rotation shaft 11 of motor 10 is inserted in bearing 203 of stem portion 20. This eccentric shaft 30 has a weight 300 in the vicinity of bearing 203, and the center of gravity of eccentric shaft 30 is offset from the center of rotation. It is noted that a minute clearance is provided between the tip end of eccentric shaft 30 and bearing 203.

<Driving Principle of Electric Toothbrush>

CPU 120 supplies a driving signal (for example, a pulse width modulation signal) in accordance with operation mode to motor 10 to rotate rotation shaft 11 of motor 10. Eccentric shaft 30 also rotates along with the rotation of rotation shaft 11, where eccentric shaft 30 moves such that it turns around the center of rotation because the center of gravity is offset. Therefore, the tip end of eccentric shaft 30 repeatedly collides against the inner wall of bearing 203 to allow stem portion 20 and brush part 21 attached thereto to vibrate (move) at high speed. In other words, motor 10 acts as driving means for vibrating (moving) the brush and eccentric shaft 30 acts as a motion transmission mechanism (motion conversion mechanism) for converting output (rotation) of motor 10 into vibration of vibrating member 2.

The user can perform brushing by holding body 1 in hand and placing the fast-vibrating brush 210 against teeth. It is noted that CPU 120 monitors the operation duration time using timer 122 and automatically stops the vibration of the brush after a lapse of a prescribed time (for example two minutes).

In the electric toothbrush in the present embodiment, eccentric shaft 30 which is a motion transmission mechanism is contained in vibrating member 2, and in particular, weight 300 is arranged in the vicinity of brush 210. Therefore, the part of brush 210 can be vibrated efficiently. On the other hand, since vibrating member 2 (stem portion 20) is mounted on body 1 with elastic member 202 interposed, vibration of vibrating member 2 is hardly transferred to body 1. This can reduce vibration of body 1 and the hand during brushing of teeth, thereby improving usability.

<Operation of Electric Toothbrush>

Food debris and plaque adhere in different ways depending on the kinds (maxilla/mandible, molar/incisor, etc.) and portions (tongue-side/cheek-side, tooth surface/occlusal surface) of teeth. Therefore, effective brushing operations, for example, such as how to apply the brush (brush angle or brush pressure), how to move the brush, speed, and brushing time, are different for each section of dentition. Furthermore, even when the kind of teeth is the same, the brush is applied in opposite directions between left and right dentitions.

Therefore, the electric toothbrush in the present embodiment estimates a section being brushed based on the orientation of the brush which is detected by acceleration sensor 15, and automatically switches operation mode (rotational direction, rotational speed, and the like) of motor 10 depending on the section being brushed.

Figure 4:
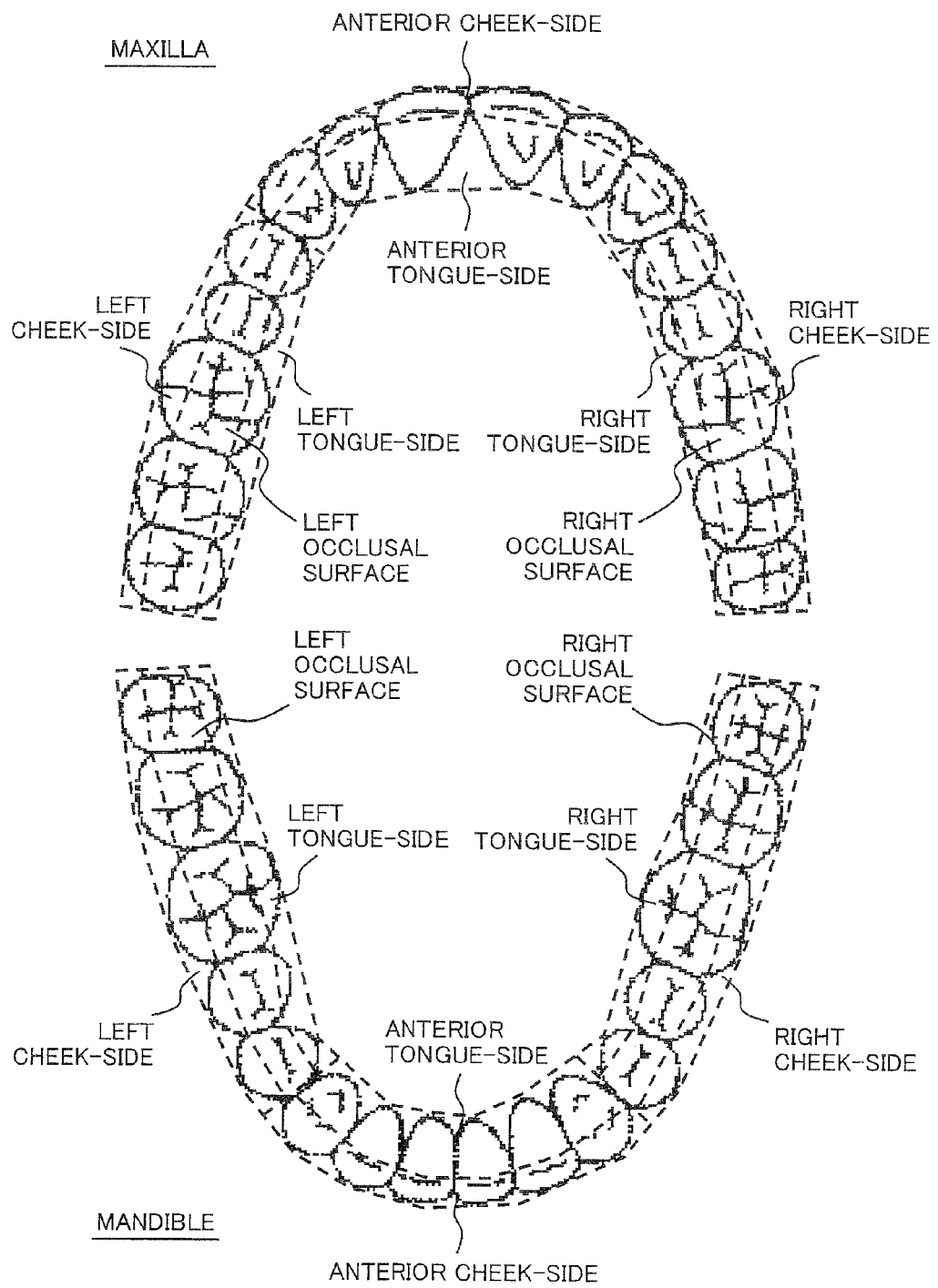
FIG. 4 is diagram showing segmentation of section being brushed.

In the present embodiment, as shown in FIG. 4, the upper and lower dentitions are segmented into 16 sections of "maxillary anterior cheek-side," "maxillary anterior tongue-side," "maxillary left cheek-side," "maxillary left tongue-side," "maxillary left occlusal surface," "maxillary right cheek-side," "maxillary right tongue-side," "maxillary right occlusal surface," "mandibular anterior cheek-side," "mandibular anterior tongue-side," "mandibular left cheek-side," "mandibular left tongue-side," "mandibular left occlusal surface," "mandibular right cheek-side," "mandibular right tongue-side," and "mandibular right occlusal surface." However, the segmentation of dentition is not limited the above-noted one and the dentition may be segmented more largely or segmented more finely.

Figure 5:
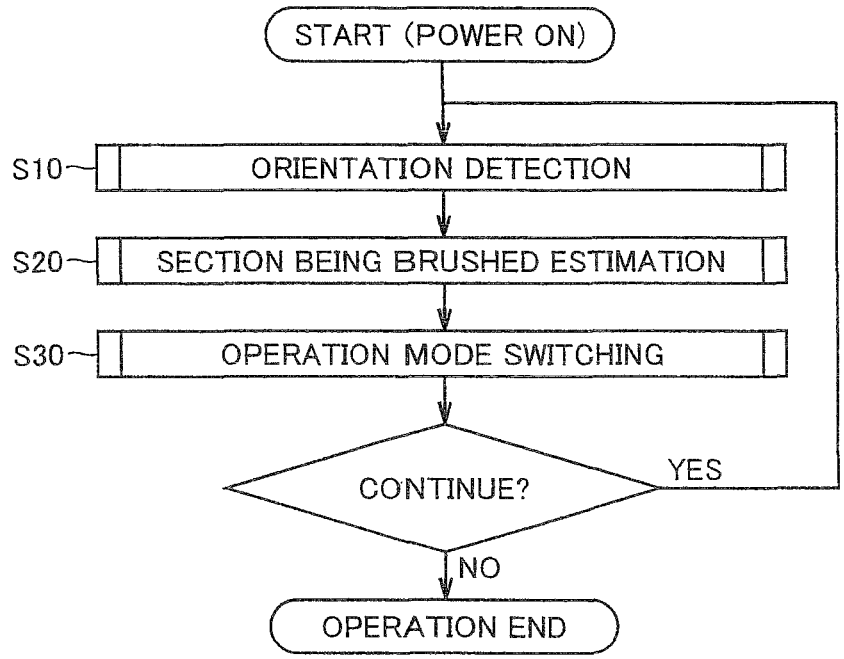
FIG. 5 is a flowchart showing a main routine of operation mode automatic control in the first embodiment.

Referring to the flowcharts in FIG. 5 to FIG. 9, the flows of operation mode automatic control will be described specifically. FIG. 5 is a flowchart of a main routine, and FIG. 6 to FIG. 9 are flowcharts showing details of each process of the main routine. It is noted that the processes described below are the processes executed by CPU 120 in accordance with a program, unless otherwise specified.

When the electric toothbrush is powered on, CPU 120 detects an orientation (inclination) of the brush based on output of acceleration sensor 15 (S10). Then, CPU 120 estimates a section being brushed based on the orientation detected in S10 (S20). Then, CPU 120 performs control to switch operation mode in accordance with the section being brushed estimated in S20 (S30). The processes in S10-S30 are repeatedly executed at certain time intervals, and the operation mode is changed as appropriate every time the section being brushed is changed. When the power is turned off, or when an operation duration time reaches a prescribed time (for example, two minutes), or when operation mode is switched manually, the main routine in FIG. 5 is ended. In the following, the processes in S10-S30 will be described in detail.

<Detection of Orientation>

Figure 6:
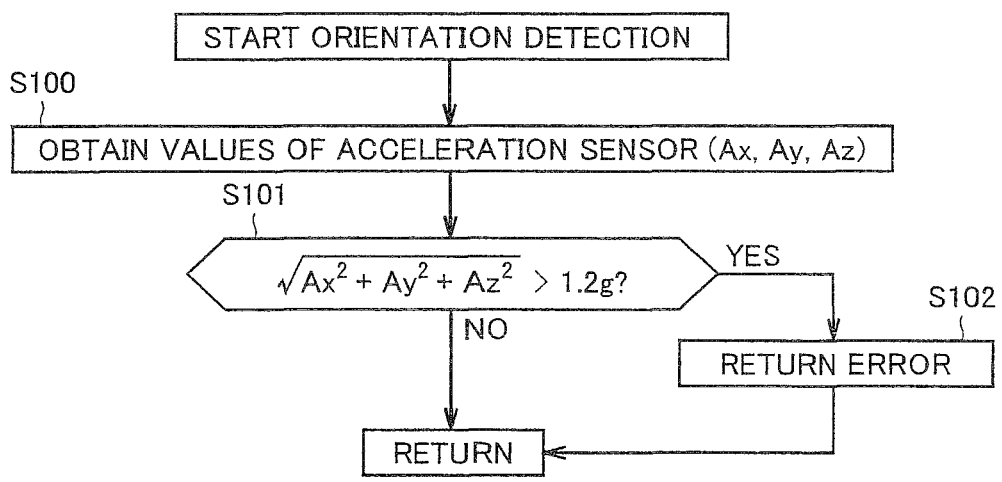
FIG. 6 is a flowchart of an orientation detection process in the first embodiment.

FIG. 6 is a flowchart of an orientation detection process (S10).

CPU 120 obtains outputs Ax, AY, Az of x, y, z, respectively, from acceleration sensor 15 (S100). Ax represents an acceleration component in the x direction. Ay represents an acceleration component in the y direction. Az represents an acceleration component in the z direction. When the toothbrush is in a still state (when dynamic acceleration does not act on acceleration sensor 15), composite vector A of Ax, Ay, Az is equivalent to gravitational acceleration. Here, A=(Ax, Ay, Az) is called an orientation vector.

Here, if the magnitude of the orientation vector A=(Ax, Ay, Az) is greater than 1.2 g (g is the gravitational acceleration) (S101; YES), an error is returned (S102). This is because the inclusion of a large amount of dynamic acceleration component in the acceleration sensor output makes it difficult to accurately specify the direction of the gravitational acceleration (that is, the three-dimensional orientation of the brush). It is noted that instead of returning an error as in S102, the processes in S100 and S101 may be repeated until acceleration sensor outputs Ax, Ay, Az are obtained in which the magnitude of composite vector is 1.2 g or less. It is noted that the threshold value in error determination is not limited to 1.2 g and may be any other value.

<Estimation of Section being Brushed>

Figure 7:
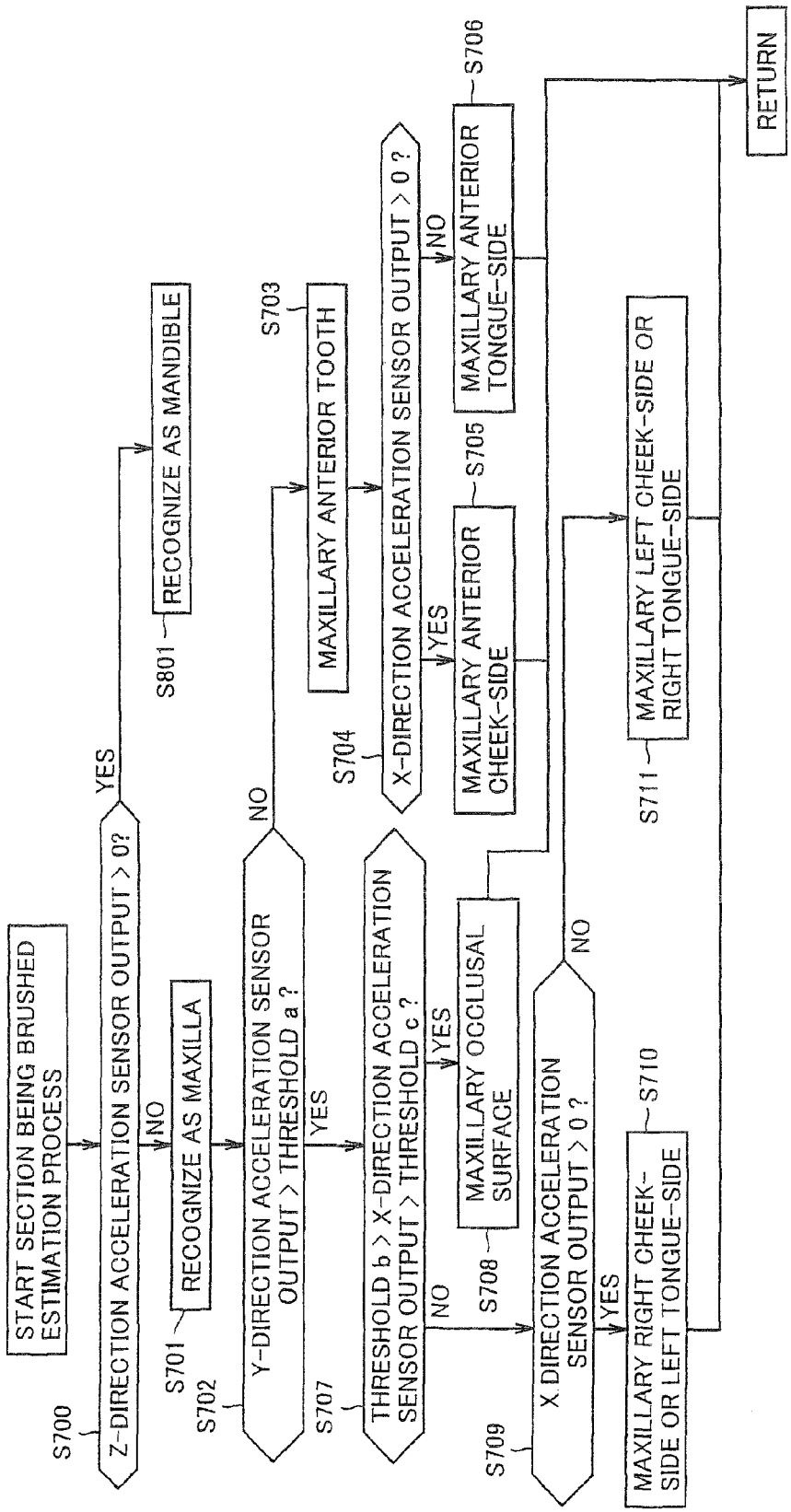
FIG. 7 is a flowchart of a section being brushed estimation process (maxilla) in the first embodiment.
Figure 8:
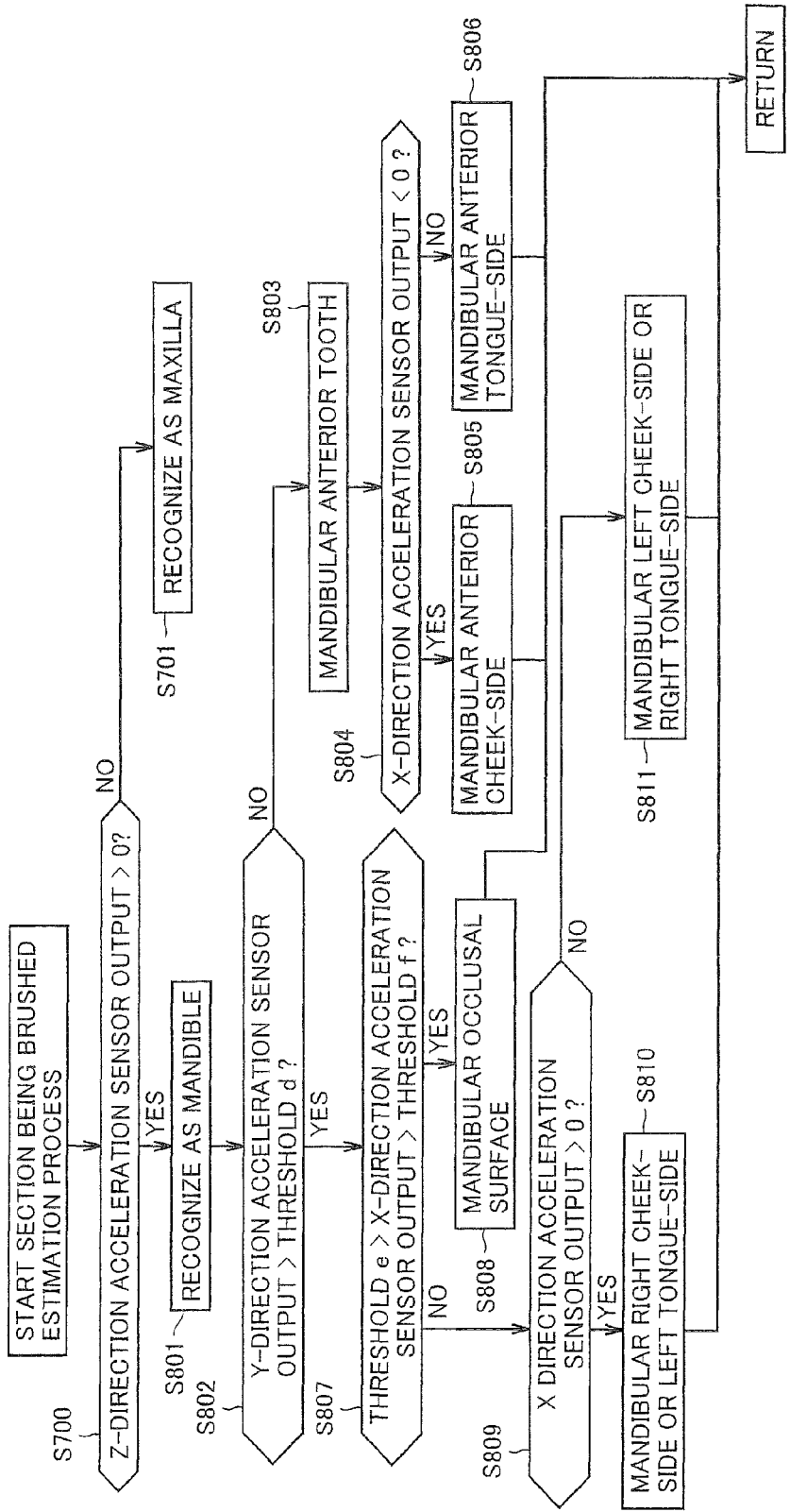
FIG. 8 is a flowchart of a section being brushed estimation process (mandible) in the first embodiment.
Figure 10:
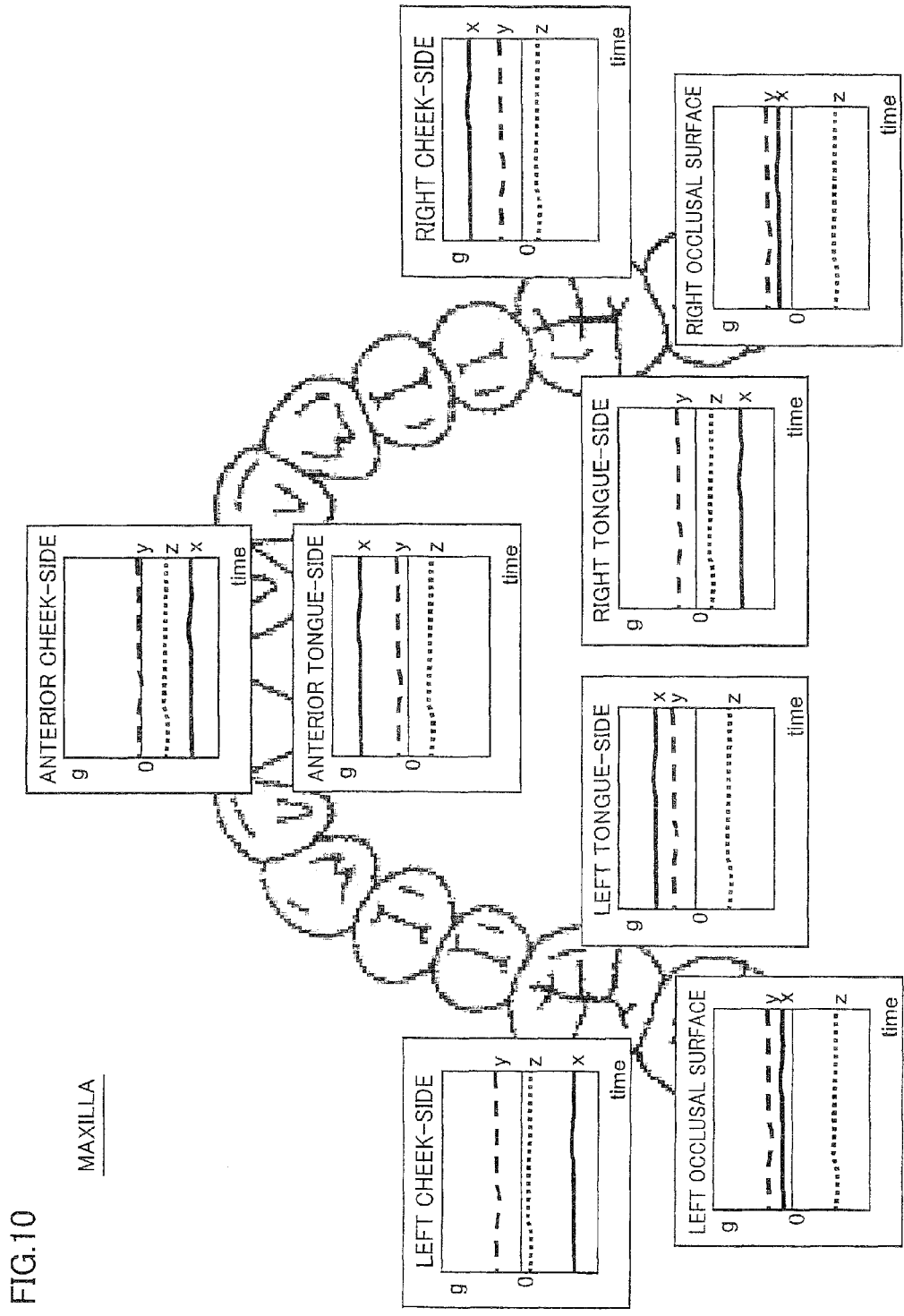
FIG. 10 is a diagram showing an example of acceleration sensor outputs Ax, Ay, Az for each section being brushed of the maxilla.
Figure 11:
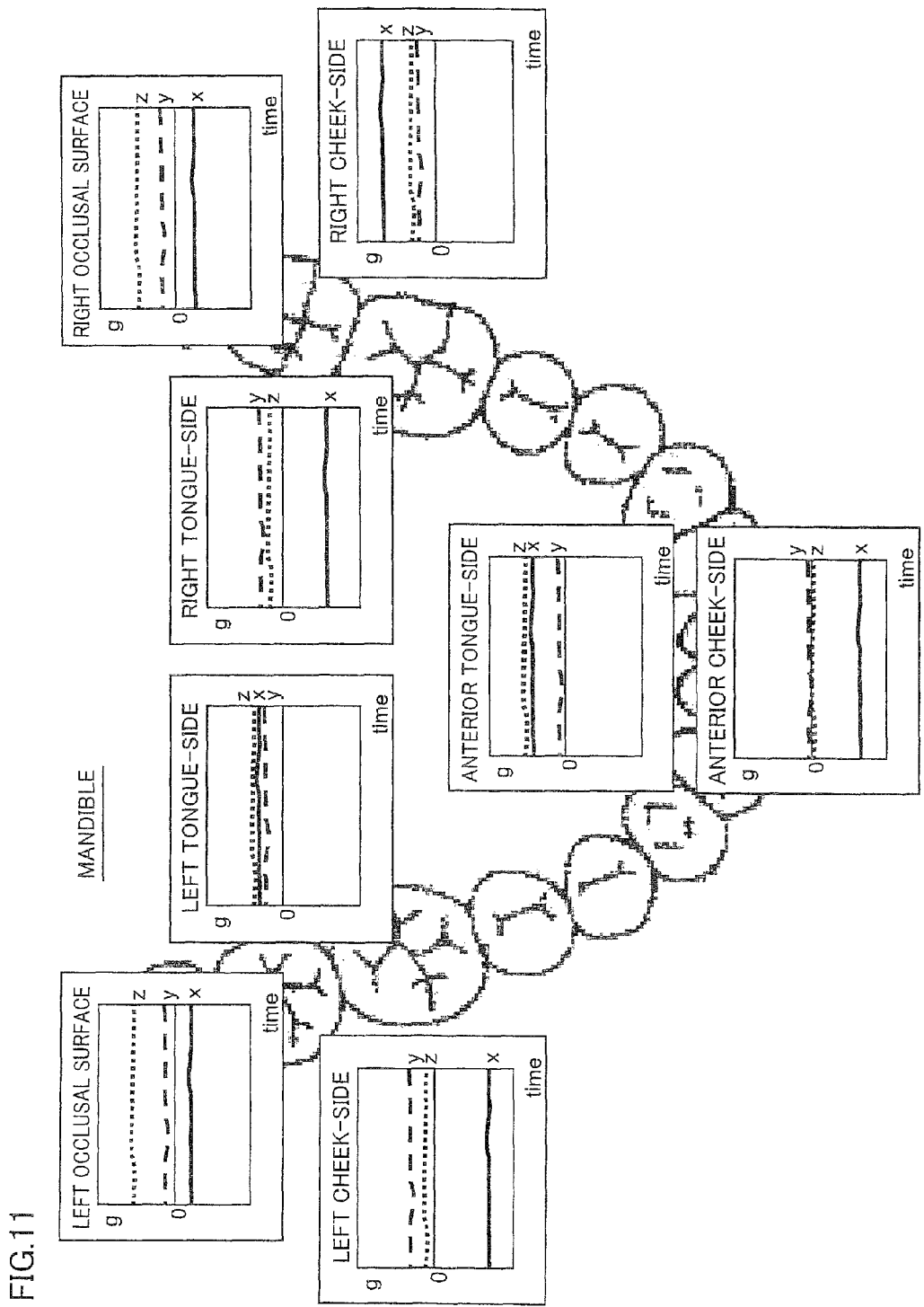
FIG. 11 is a diagram showing an example of acceleration sensor outputs Ax, Ay, Az for each section being brushed of the mandible.

FIG. 7 and FIG. 8 are flowcharts of a section being brushed estimation process (S20). FIG. 10 and FIG. 11 are diagrams showing an example of acceleration sensor outputs Ax, Ay, Az for each section being brushed.

First, CPU 120 determines whether maxilla or mandible based on the output Az of the acceleration sensor in the z direction (S700). This determination is based on the notion that the brush face mostly faces up in brushing the maxillary dentition and the brush face mostly faces down in brushing the mandibular dentition. If Az>0, it is determined as being mandible (S801). If Az≤0, it is determined as being maxilla (S701).

(1) In the Case of Maxilla

CPU 120 determines whether an anterior tooth or not based on the output Ay of the acceleration sensor in the y direction (S702). This determination is based on the notion that toothbrush body 1 is relatively horizontally oriented in brushing anterior teeth while toothbrush body 1 is forced to be obliquely oriented in brushing molars as it interferes with lips. If Ay≤threshold value a, it is determined as being a maxillary anterior tooth (S703).

If it is determined as being a maxillary anterior tooth, CPU 120 determines whether the cheek-side or the tongue-side based on the output Ax of the acceleration sensor in the x direction (S704). This determination is made based on the notion that the brush is oriented in opposite directions between the cheek-side and the tongue-side. If Ax>0, it is determined as being "maxillary anterior cheek-side" (S705), and if Ax≤0, it is determined as being "maxillary anterior tongue-side" (S706).

On the other hand, if it is determined as not being a maxillary anterior tooth in S702, CPU 120 determines whether an occlusal surface or not based on the output Ax of the acceleration sensor in the x direction (S707). This determination is made based on the notion that the brush face is generally horizontally oriented in brushing an occlusal surface and the output Ax is extremely small. If threshold value b>Ax>threshold value c, it is determined as being "maxillary left occlusal surface or maxillary right occlusal surface" (S708). It is noted that in the first embodiment the maxillary left occlusal surface and the maxillary right occlusal surface are not specifically distinguished from each other. This is because in the case of the occlusal surface, there is no great necessity for changing the brushing operation between left and right.

If Ax≥threshold value b or Ax≤threshold value c, CPU 120 determines whether the cheek-side or the tongue-side, depending on whether Ax is greater than zero or not (S709). This determination is based on the notion that the brush is oriented in opposite directions between the cheek-side and the tongue-side. If Ax>0, it is determined as being "maxillary right cheek-side or maxillary left tongue-side" (S710). If Ax≤0, it is determined as being "maxillary left cheek-side or maxillary right tongue-side" (S711). It is noted that in the first embodiment the maxillary right cheek-side and the maxillary left tongue-side are not specifically distinguished from each other. This is because there is no great necessity for changing the brushing operation between those sections. This is applicable to the maxillary left cheek-side and the maxillary right tongue-side.

(2) In the Case of Mandible

CPU 120 determines whether an anterior tooth or not based on output Ay of the acceleration sensor in the y direction (S802). This determination is based on the notion that toothbrush body 1 is relatively horizontally oriented in brushing anterior teeth while toothbrush body 1 is forced to be obliquely oriented in brushing molars as it interferes with lips. If Ay≤threshold value d, it is determined as being a mandibular anterior tooth (S803).

If it is determined as being a mandibular anterior tooth, CPU 120 determines whether the cheek-side or the tongue-side based on the output Ax of the acceleration sensor in the x direction (S804). This determination is made based on the notion that the brush is oriented in opposite directions between the cheek-side and the tongue-side. If Ax<0, it is determined as being "mandibular anterior cheek-side" (S805), and if Ax≥0, it is determined as being "mandibular anterior tongue-side" (S806).

On the other hand, if it is determined as not being a mandibular anterior tooth in S802, CPU 120 determines whether an occlusal surface or not based on the output Ax of the acceleration sensor in the x direction (S807). This determination is made based on the notion that the brush face is generally horizontally oriented in brushing an occlusal surface and the output Ax is extremely small. If threshold value e>Ax>threshold value f, it is determined as being "mandibular left occlusal surface or mandibular right occlusal surface" (S808). It is noted that in the first embodiment the mandibular left occlusal surface and the mandibular right occlusal surface are not specifically distinguished from each other. This is because in the case of the occlusal surface, there is no great necessity for changing the brushing operation between left and right.

If Ax≥threshold value e or Ax≤threshold value f, CPU 120 determines whether the cheek-side or the tongue-side depending on whether Ax is greater than zero or not (S809). This determination is based on the notion that the brush is oriented in opposite directions between the cheek-side and the tongue-side. If Ax>0, it is determined as being "mandibular right cheek-side or mandibular left tongue-side" (S810). If Ax≤0, it is determined as being "mandibular left cheek-side or mandibular right tongue-side" (S811). It is noted that in the first embodiment the mandibular right cheek-side and the mandibular left tongue-side are not specifically distinguished from each other. This is because there is no great necessity for changing the brushing operation between those parts. This is applicable to the mandibular left cheek-side and the mandibular right tongue-side.

Through the processes as described above, the currently section being brushed is specified as any one of "maxillary anterior cheek-side" (S705), "maxillary anterior tongue-side" (S706), "maxillary occlusal surface" (S708), "maxillary right cheek-side or maxillary left tongue-side" (S710), "maxillary left cheek-side or maxillary right tongue-side" (S711), "mandibular anterior cheek-side" (S805), "mandibular anterior tongue-side" (S806), "mandibular occlusal surface" (S808), "mandibular right cheek-side or mandibular left tongue-side" (S810), and "mandibular left cheek-side or mandibular right tongue-side" (S811).

Figure 28:
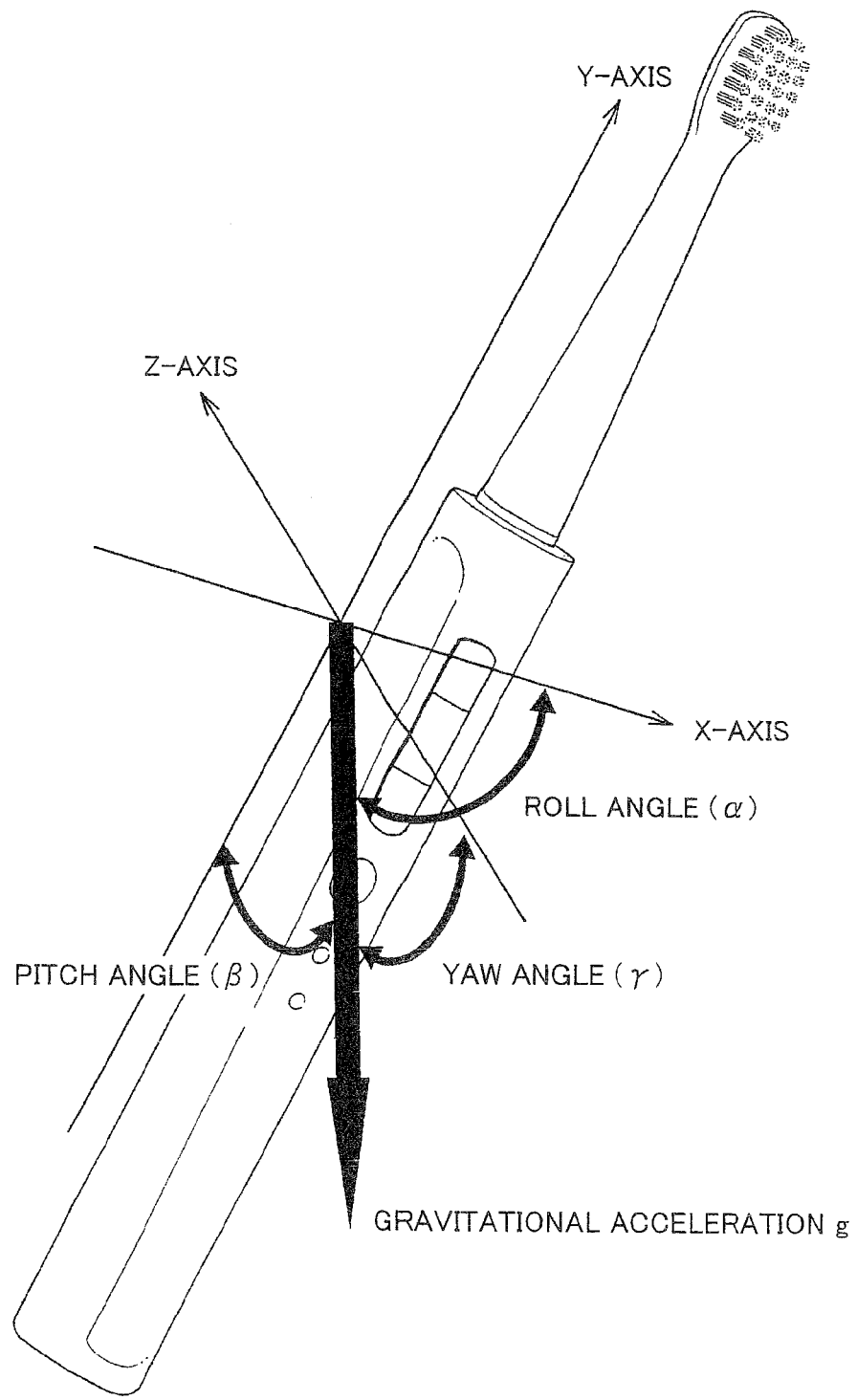
FIG. 28 is a diagram showing definitions of orientation angles of the electric toothbrush.

It is noted that the above-noted determination algorithm is shown only by way of example, and any algorithm may be employed as long as a section being brushed can be specified from the outputs Ax, Ay, Az of the acceleration sensor. For example, determination may be made not using the values of Ax, Ay, Az as they are as the determination variables but using a secondary variable obtained by combining Ax, Ay, Az as appropriate. The secondary variable can be set as desired, for example, such as Ay/Az, Ax·Ax+Ay·Ay, Ay−Ax. Alternatively, the acceleration information for each axis Ax, Ay, Az may be converted into angular information (orientation angle) α, β, γ as shown in FIG. 28 before a section being brushed is determined. In the example in FIG. 28, the angle in the x-axis with respect to the gravitational acceleration direction, the angle in the y-axis with respect to the gravitational acceleration direction, and the angle in the z-axis with respect to the gravitational acceleration direction are defined as a roll angle α, a pitch angle β, and a yaw angle γ, respectively. The threshold values for use in determination can be determined from clinical experiment results and the like.

<Operation Mode Switching>

In the electric toothbrush in the present embodiment, the turning motion of the eccentric shaft is used to generate vibration of the brush as described above. In the case of such driving principle, the brush vibrates along an elliptical trajectory in the plane (in the zx plane) vertical to the rotation shaft of the motor. Then, when the rotational direction of the motor is reversed, the brush follows the trajectory symmetric with respect to the yz plane since the vibrating mechanism of the toothbrush is symmetric with respect to the yz plane.

Figure 12:
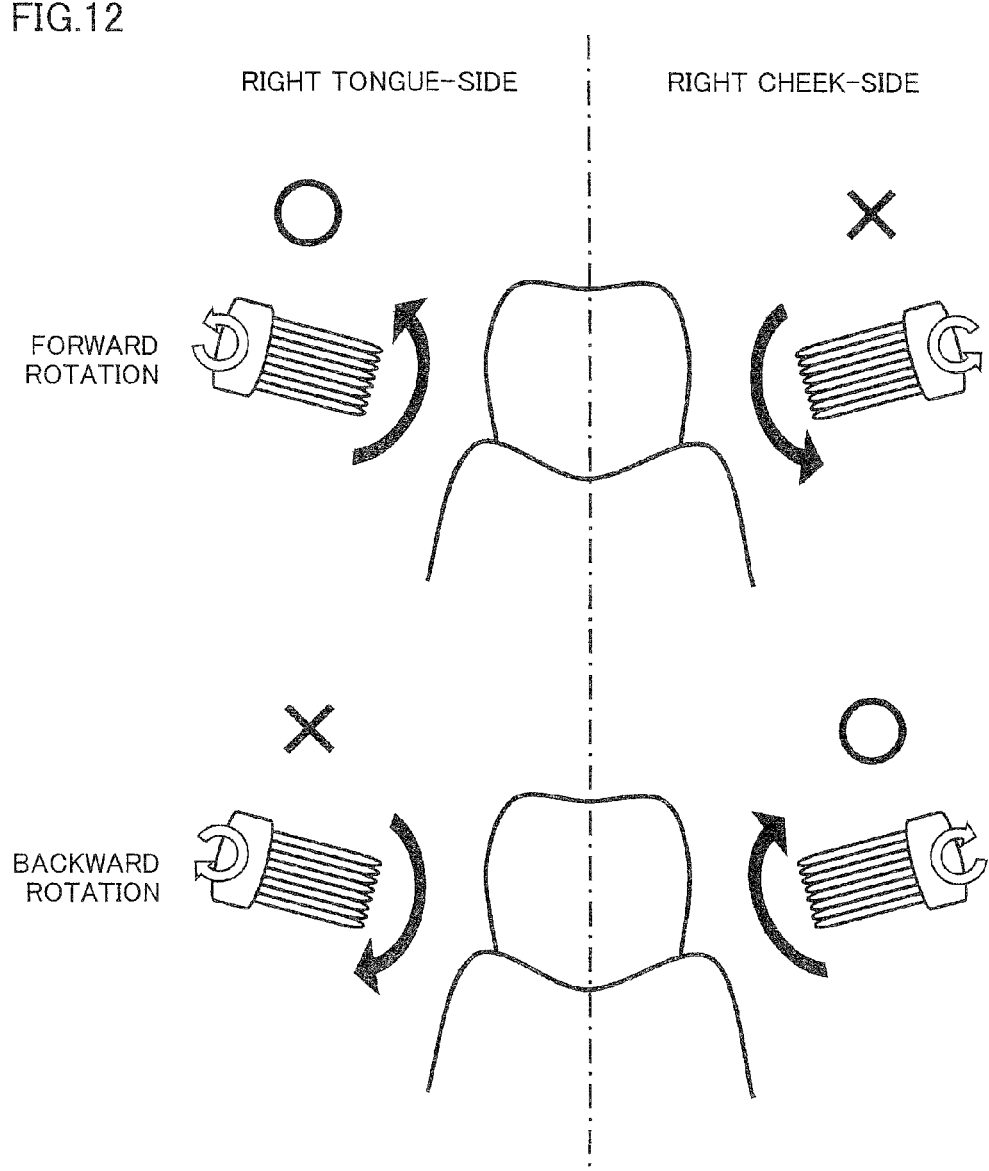
FIG. 12 is a diagram schematically showing a rotational direction of a motor and a movement of a brush.

FIG. 12 schematically shows a rotational direction of the motor and a movement of the brush. When the motor is rotated forward, the bristles of the brush move in such a manner as to scrape off plaque from periodontal pockets at the mandibular right tongue-side whereas the bristles of the brush move in such a manner as to push plaque into periodontal pockets at the mandibular right cheek-side. Therefore, it can be understood that it is desired to rotate the motor forward when the mandibular right tongue-side is brushed. On the other hand, it can be understood that it is desired to rotate the motor backward so that the bristles of the brush move to scrape off plaque when the mandibular right cheek-side is brushed. Based on such findings, in the present embodiment, the rotational direction (forward rotation/backward rotation) of the rotation motor is switched depending on a section being brushed.

Figure 9:
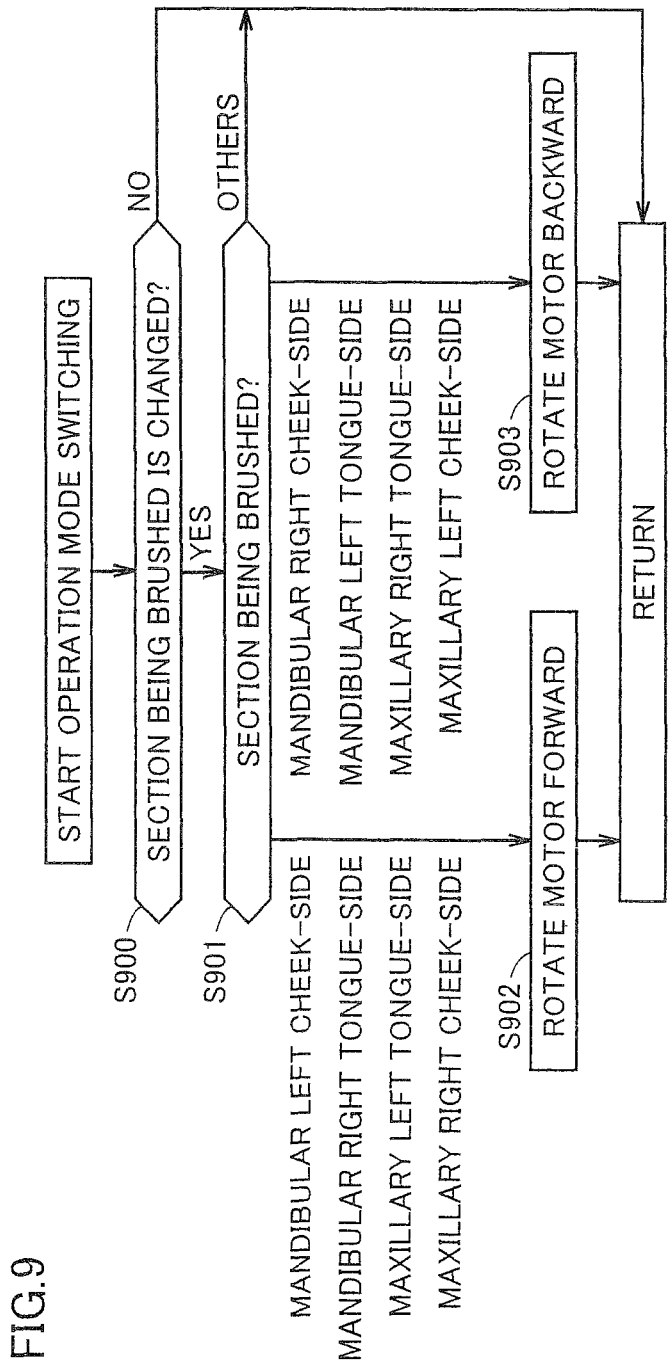
FIG. 9 is a flowchart of an operation mode switching process in the first embodiment.

FIG. 9 is a flowchart of an operation mode switching process (S30), CPU 120 checks whether the section being brushed is changed or not by comparing the section being brushed specified in S20 with the section being brushed in the previous process (the process one clock earlier) (S900). It is noted that the section being brushed in the previous process is stored in the memory.

When the section being brushed is changed (S900; YES), CPU 120 determines which group the currently section being brushed falls in, of a first group "mandibular left cheek-side, mandibular right tongue-side, maxillary left tongue-side, maxillary right cheek-side" and a second group "mandibular right cheek-side, mandibular left tongue-side, maxillary right tongue-side, maxillary left cheek-side" (S901). Then, if in the first group, CPU 120 sets the rotational direction of the motor to forward rotation (S902). If in the second group, CPU 120 sets the rotational direction of the motor to backward rotation (S903).

In this manner, the rotational direction of the motor is controlled such that an appropriate and effective movement of brush bristles that is suitable for a section being brushed is realized, thereby improving plaque removing power.

Second Embodiment

The electric toothbrush in a second embodiment of the present invention will now be described. In the first embodiment, the rotational direction of the motor is controlled depending on a section being brushed. In the second embodiment, the frequency (motion frequency, specifically, a rotational speed of the motor) of the brush is controlled depending on a section being brushed. The other structure is similar to that of the first embodiment and therefore a structure specific to the present embodiment will mainly be described below.

Figure 13:
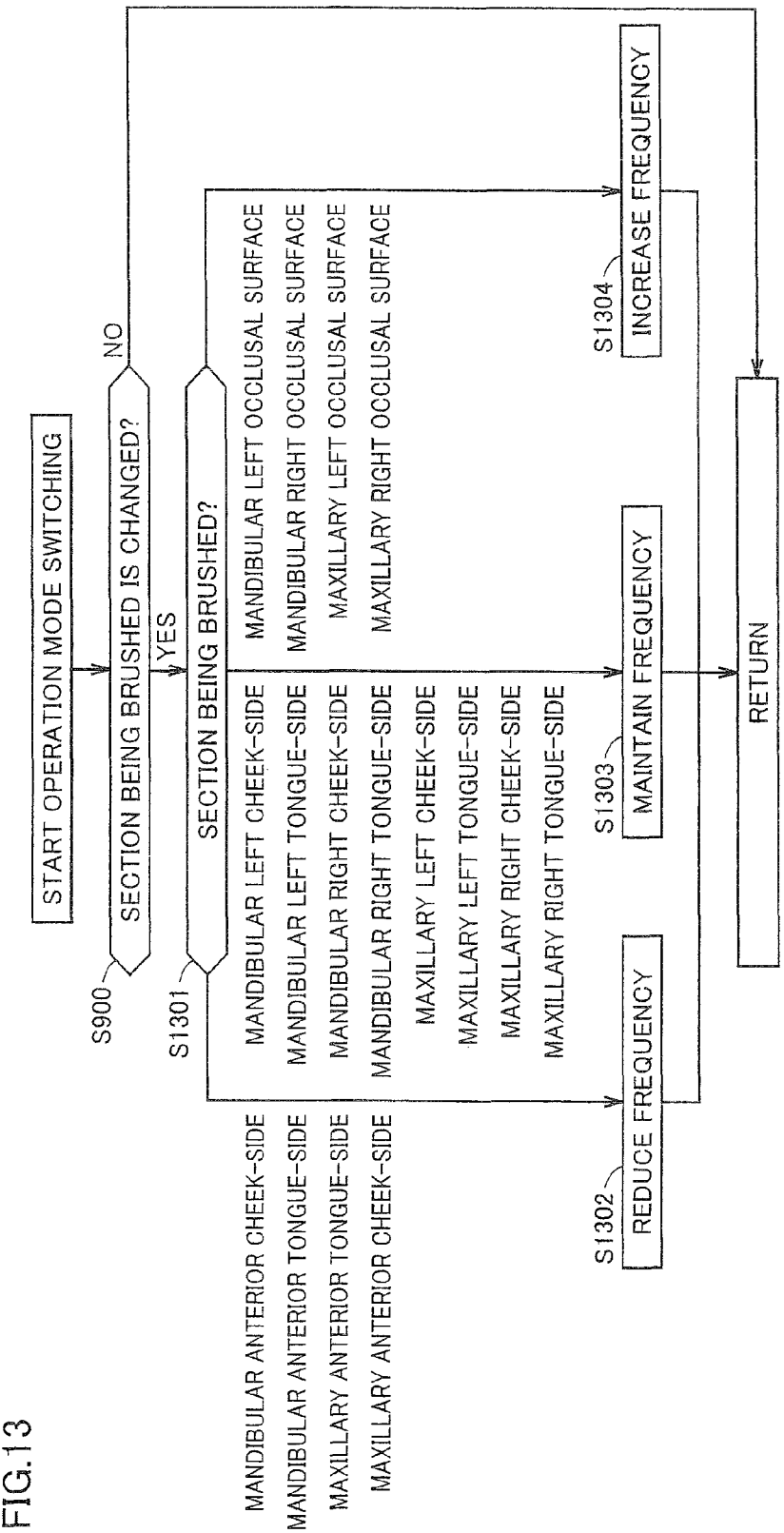
FIG. 13 is a flowchart of an operation mode switching process in a second embodiment.

FIG. 13 is a flowchart of an operation mode switching process (S30 in FIG. 5) in the second embodiment. CPU 120 checks whether the section being brushed is changed or not by comparing the section being brushed specified in S20 with the section being brushed in the previous process (the process one clock earlier) (S900). It is noted that the section being brushed in the previous process is stored in the memory.

If the section being brushed is changed (S900; YES), CPU 120 determines which group the currently section being brushed falls in, of a first group "mandibular anterior cheek-side, mandibular anterior tongue-side, maxillary anterior cheek-side, maxillary anterior tongue-side," a second group "mandibular left cheek-side, mandibular left tongue-side, mandibular right cheek-side, mandibular right tongue-side, maxillary left cheek-side, maxillary left tongue-side, maxillary right cheek-side, maxillary right tongue-side," and a third group "mandibular left occlusal surface, mandibular right occlusal surface, maxillary left occlusal surface, maxillary right occlusal surface" (S1301). The first group is a section where gums are sensitive and where much strong brushing is not preferable. The third group is a section where the brush does not touch on gums and a high brushing effect is desired.

In the case of the first group, CPU 120 controls the rotational speed of the motor such that the brush vibrates at a frequency one step lower than the current setting value (S1302). In the case of the second group, CPU 120 controls the rotational speed of the motor such that the brush vibrates at a frequency of the current setting value (S1303). In the case of the third group, CPU 120 controls the rotational speed of the motor such that the brush vibrates at a frequency one step higher than the current setting value (S1304). For example, in a toothbrush in which frequencies can be switched in five steps, when the current setting value is "3," brushing of the first group is performed at a frequency of "2," brushing of the second group is performed at a frequency of "3," and brushing of the third group is performed at a frequency of "4."

Accordingly, the brushing strength can be set weak for the section where gums are sensitive. Conversely, the brushing strength can be set strong for the section where a high brushing effect is desired. Therefore, the brushing effect and the sense of medical treatment can be improved.

Although in the present embodiment the frequency of the brush is controlled with attention being given to stimuli to gums for each section being brushed, the frequency of the brush can be controlled for any other purpose. For example, noting that the contact areas between the brush and teeth are different among section being brushed, control may be performed such that the brushing effect is enhanced by increasing the frequency for a section having a large contact surface (for example, the maxillary anterior cheek-side, the occlusal surface, and the like) while the frequency is decreased for a section having a small contact surface (for example, the mandibular left tongue-side, maxillary right cheek-side, and the like). Although in the present embodiment the frequencies are controlled in three steps, the frequencies may be changed in two steps or in four or more steps.

When the driving speed (frequency or rotational speed) of the brush is changed, the driving speed may be changed rapidly as shown in the upper graph in FIG. 29. However, a sudden change or frequent changes of driving speed during brushing may give the user uncomfortable feeling or may cause unstable control. Then, as shown in the lower graph in FIG. 29, it is also preferable to perform such control in that the driving speed changes gradually (or step by step). For example, the rotational speed of the motor may be controlled such that the speed changing rate does not reach a certain setting value or higher.

Third Embodiment

The electric toothbrush in a third embodiment of the present invention will now be described. In the present embodiment, CPU 120 estimates a brush angle based on the orientation of the brush and switches operation mode in accordance with the section being brushed and the brush angle. The other structure is similar to that of the forgoing embodiments and therefore a structure specific to the present embodiment will mainly be described below.

<Vibration Characteristics>

In this electric toothbrush, the turning motion of the eccentric shaft is utilized to generate vibration of the brush. The brush vibrates along an elliptical trajectory in the plane vertical to the rotation shaft of the motor. The present inventors have observed and analyzed vibration of the brush with various frequencies (motor rotational speeds) and found that this electric toothbrush has the following vibration characteristics.

(1) The brush portion has at least two resonance points (resonance frequencies).

(2) The resonance direction at each resonance point is different from another. Specifically, as shown in FIG. 14, at a resonance point (first resonance: about 12500 spm) on the lower frequency side, the amplitude in the x-axis direction parallel to the brush face increases. At a resonance point (second resonance: about 38000 spm) on the higher frequency side, the amplitude in the z-axis direction vertical to the brush face increases. Out of resonance (for example, about 26500 spm), the brush follows a trajectory oblique (about 45 degrees) with respect to the x-axis (the z-axis). Here, "spm" is a unit representing the number of swings per minute.

The reason why a plurality of resonances that are different in direction appear may be that they are heavily dependent on the structure of the electric toothbrush or the driving principle thereof. The present inventors have repeated experiments with various eccentric shafts and brush structures and then made a finding that the first resonance point is characterized by being mainly dependent on the motion transmission mechanism and that the second resonance point is characterized by being mainly dependent on the brush. In other words, it has been found that the frequency and amplitude of the first resonance point can be adjusted by changing the structure and shape of the motion transmission mechanism (simply, the position, size, weight, etc. of the weight of the eccentric shaft), and that the frequency and amplitude of the second resonance point can be adjusted by changing the structure and shape of the brush.

<Brush Angle>

Figure 15:
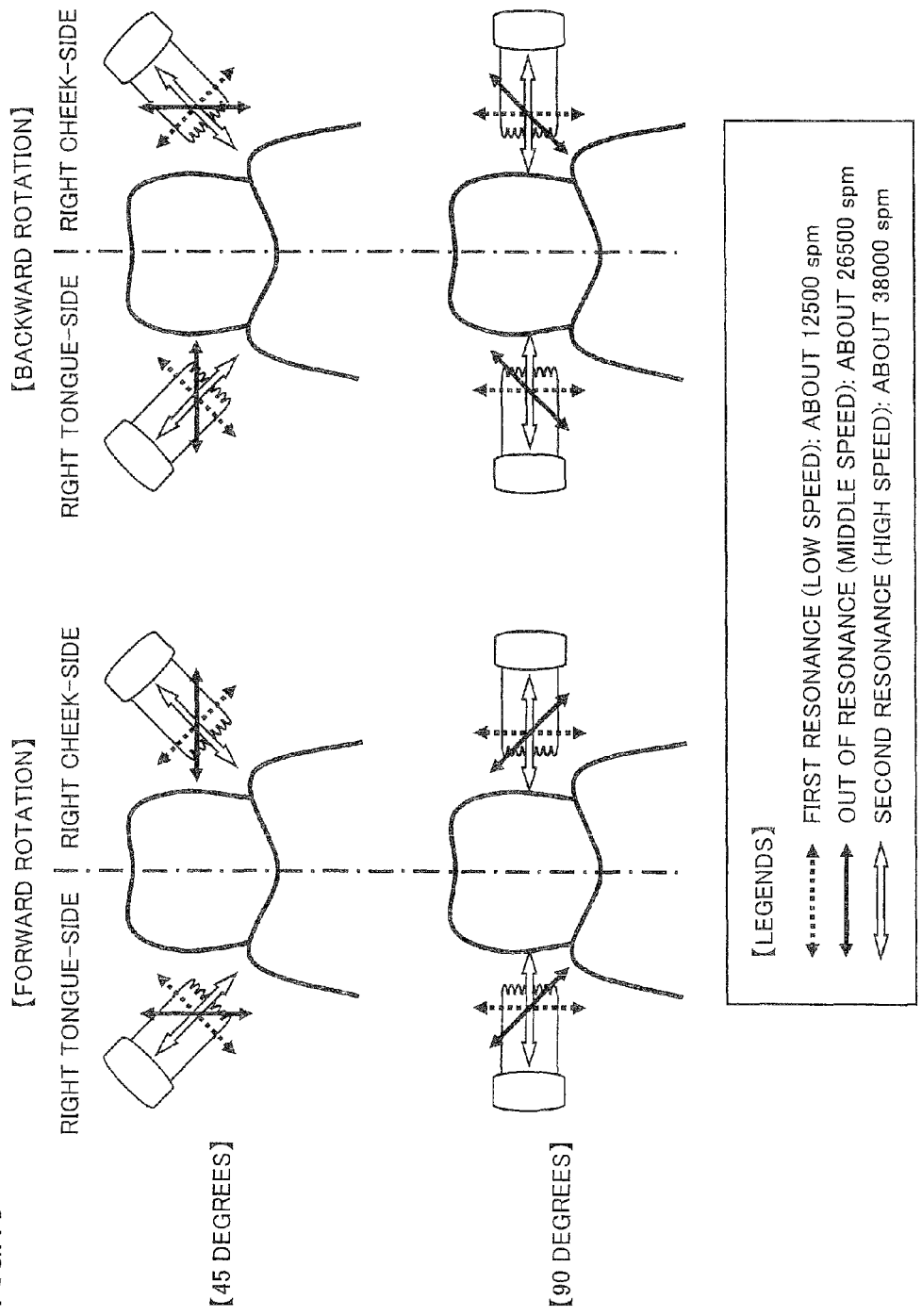
FIG. 15 is a diagram showing a relation between a brush angle and a brush movement.

A brush angle refers to an application angle of a brush with respect to a tooth axis (the axis along the head and root of a tooth). The upper figures in FIG. 15 show the states of brush angle=45 degrees and the lower figures in FIG. 15 show the states of brush angle=90 degrees. The left figures in FIG. 15 show the states in which the motor rotates forward and the right figures show the states in which the motor rotates backward. Then, each arrow shows a movement of a brush (the direction in which amplitude is the largest). Generally, the brush moves traversely (the x-axis direction) at first resonance, the brush moves longitudinally (the z-axis direction) at second resonance, and the brush moves obliquely out of resonance.

In order to scrape off food debris and plaque from periodontal pockets or between teeth effectively, it is desired to move the brush such that the bristles of the brush get into periodontal pockets or between teeth. In other words, it is preferable that the direction in which the brush moves is oblique (for example, 45 degrees) to the tooth axis. Therefore, in the example in FIG. 15, it can be understood that in the case of the brush angle of 45 degrees, the movement of second resonance is most suitable. On the other hand, it can be understood that in the case of the brush angle of 90 degrees, the movement out of resonance with motor forward rotation is most suitable at the mandibular right tongue-side and the movement out of resonance with motor backward rotation is most suitable at the mandibular right cheek-side. It is noted that based on the similar concept, the optimum operation mode (motor rotational direction and brush frequency) can be determined for each combination of a section being brushed and a brush angle.

<Estimation of Brush Angle>

Figure 16:
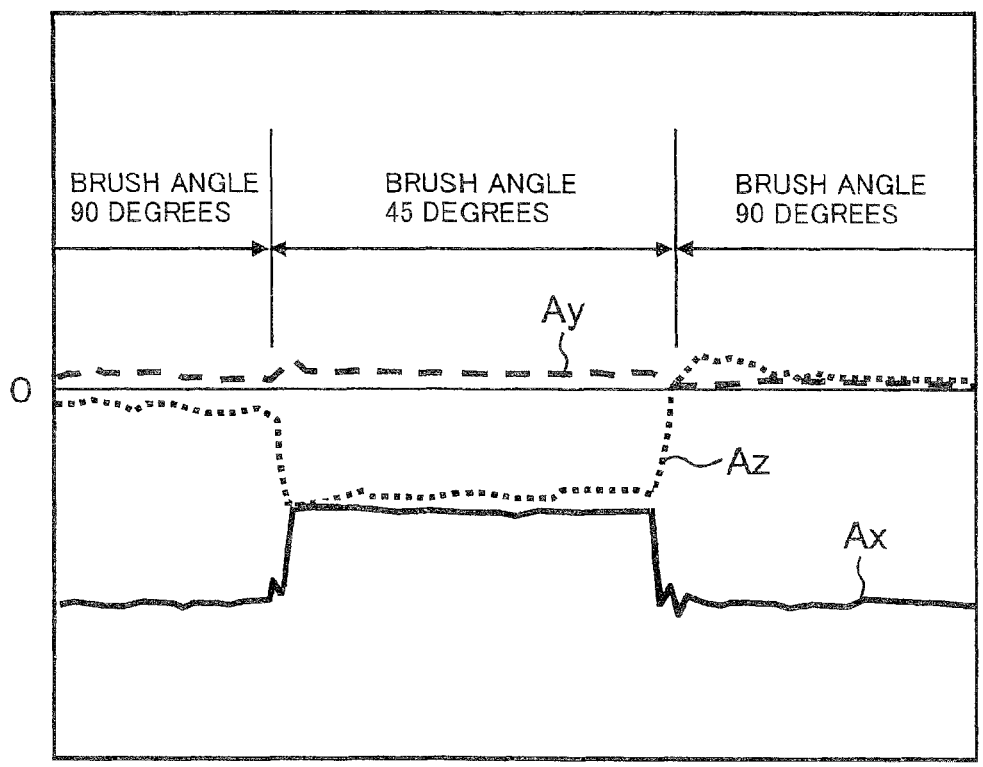
FIG. 16 is a diagram showing a waveform change of sensor output along with a changing brush angle.

The brush angle can be estimated from, for example, the acceleration component Az in the z direction. As shown in FIG. 16, when the brush angle is about 90 degrees, Az is almost zero. The smaller the brush angle is, the greater the value of Az is. In this manner, the value of Az changes significantly according to the brush angle. The acceleration component Ax in the x direction also changes according to the brush angle, and therefore it is also preferable to estimate the brush angle from Ax instead of Az or to estimate the brush angle from both of Ax and Az (the direction of composite vector of Ax and Az). Although the brush angle can be calculated based on the continuous amount, the accuracy on such a level as "about 45 degrees or about 90 degrees" is enough for operation mode switching in the present embodiment. Therefore, the brush angle is determined with a simple process of comparison between Az and a threshold value in the process as described below.

Figure 17:
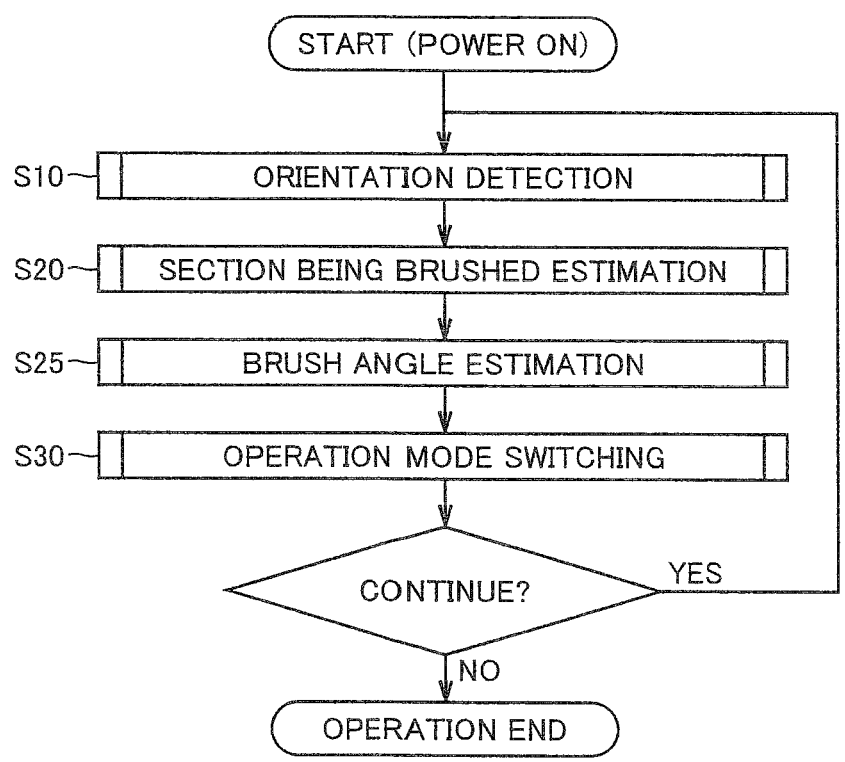
FIG. 17 is a flowchart showing a main routine of operation mode automatic control in a third embodiment.

FIG. 17 is a flowchart of a main routine in the third embodiment. It differs from the first embodiment in that a brush angle estimation process (S25) is added. In S25, CPU 120 regards the brush angle as 90 degrees, if the absolute value of Az obtained in S10 is smaller than a predetermined threshold value (if close to zero), and regards the brush angle as 45 degrees, if the absolute value of Az is equal to or greater than the threshold value. This function of CPU 120 corresponds to the brush angle estimation means in the present invention.

<Operation Mode Switching Process>

Figure 18:
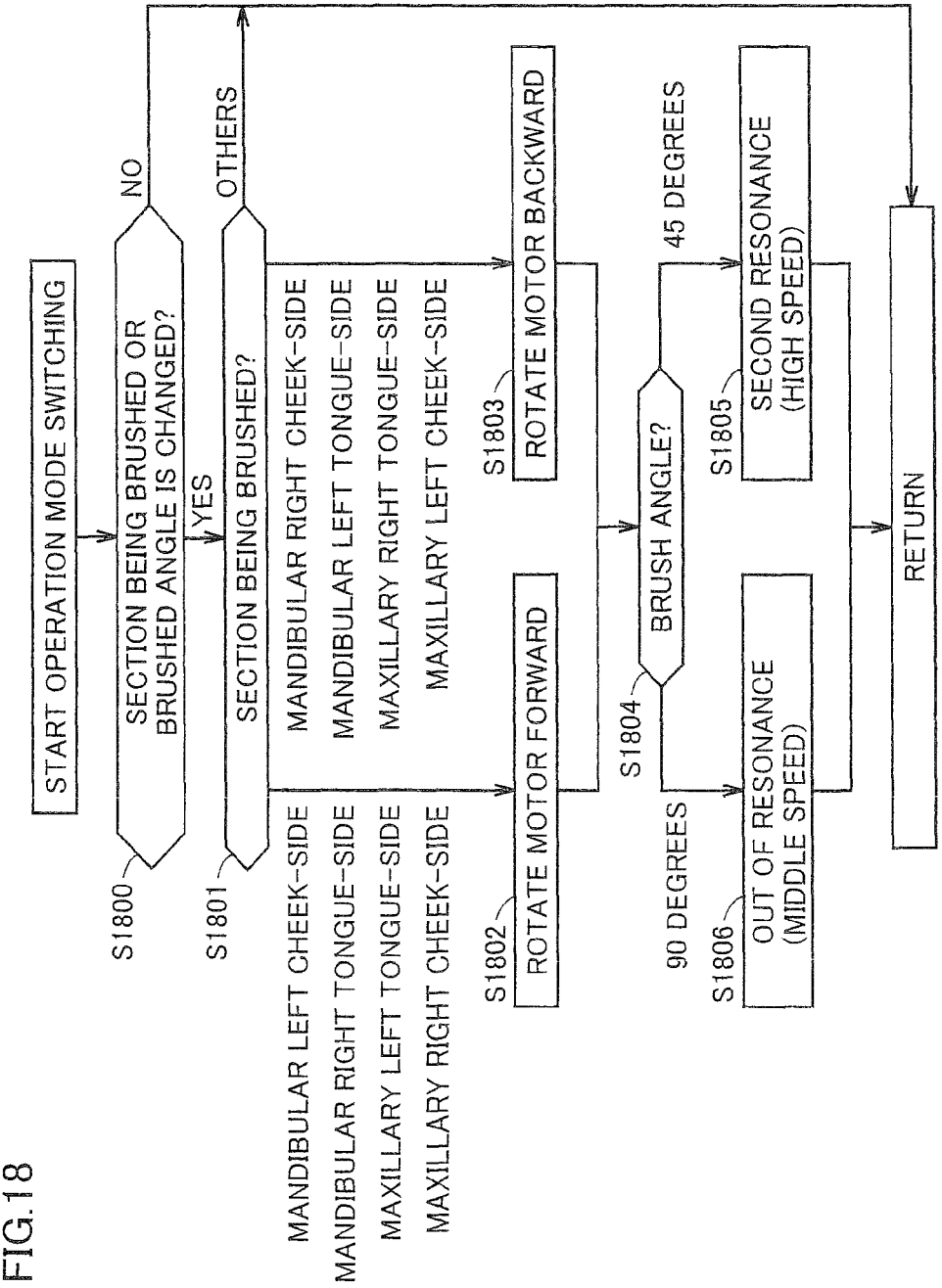
FIG. 18 is a flowchart of an operation mode switching process in the third embodiment.

FIG. 18 is a flowchart of an operation mode switching process (S30 in FIG. 17).

CPU 120 checks whether the section being brushed or the brush angle is changed by comparing the section being brushed specified in S20 and the brush angle specified in S25 with the section being brushed and the brush angle in the previous process (S1800). It is noted that the section being brushed and the brush angle in the previous process are stored in the memory.

If the section being brushed or the brush angle is changed (S1800; YES), CPU 120 determines which group the currently section being brushed falls in, of a first group "mandibular left cheek-side, mandibular right tongue-side, maxillary left tongue-side, maxillary right cheek-side" and a second group "mandibular right cheek-side, mandibular left tongue-side, maxillary right tongue-side, maxillary left cheek-side" (S1801). Then, if in the first group, CPU 120 sets the rotational direction of the motor to forward rotation (S1802). If in the second group, CPU 120 sets the rotational direction of the motor to backward rotation (S1803). Furthermore, CPU 12 controls the frequency of the brush to second resonance (high speed) if the brush angle is 45 degrees (S1804, S1805), and controls the frequency of the brush to out of resonance (middle speed) if the brush angle is 90 degrees (S1806).

According to the control in the present embodiment as described above, the movement of brush bristles that is most suitable for brushing between teeth or periodontal pockets can be realized based on the section being brushed and the brush angle, thereby even further improving plaque removing power. In this case, it is more effective to use an ultrasonic vibrating element in combination in order to kill periodontal bacteria in periodontal pockets. Although the brush angle is estimated in two steps of 45 degrees and 90 degrees, the brush angle may be estimated in three or more steps or by a continuous amount, and the frequency of the brush may also be changed in three or more steps or in a continuous manner, accordingly.

Fourth Embodiment

Figure 19:
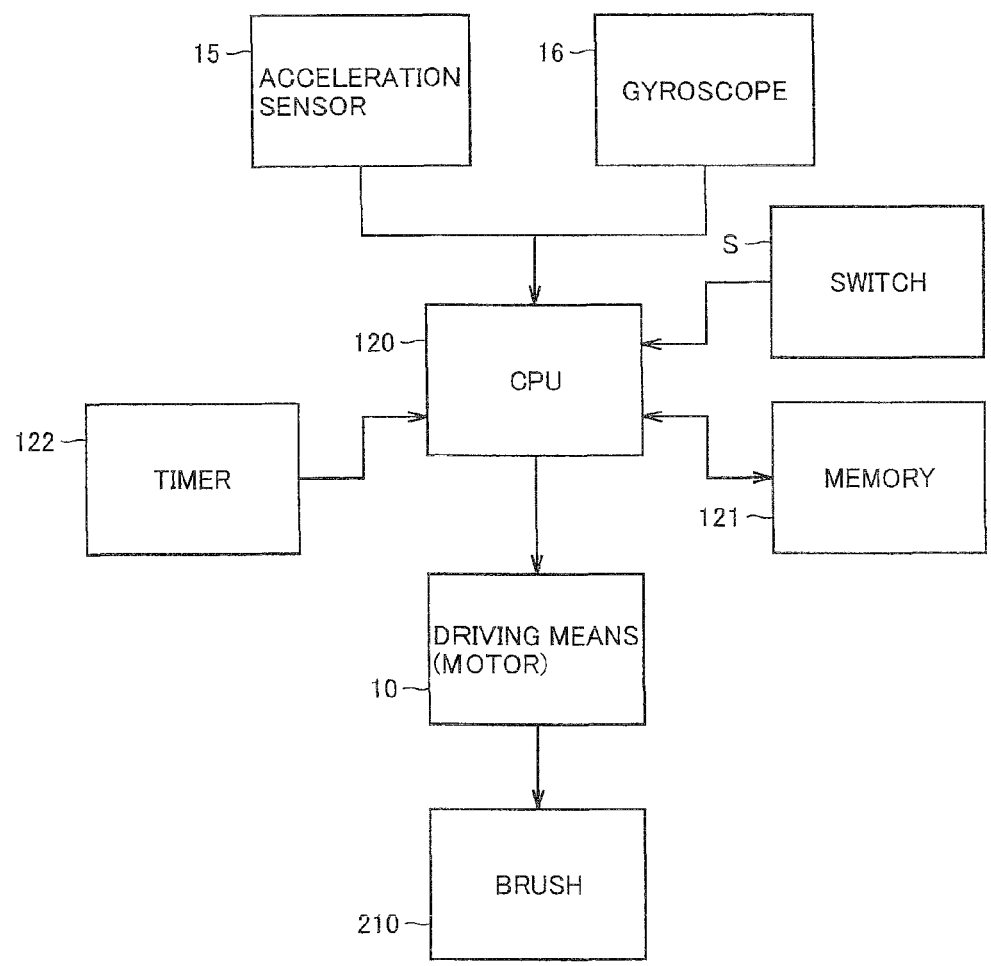
FIG. 19 is a block diagram showing an electric toothbrush in a fourth embodiment.

FIG. 19 is a block diagram of the electric toothbrush in a fourth embodiment. The electric toothbrush in the present embodiment includes a multi-axis (here, three axes) gyroscope 16 in the inside of body 1.

Gyroscope 16 is installed so as to be able to detect angular velocity around the z-axis, angular velocity around the x-axis, and angular velocity around the y-axis. A vibratory, optical, mechanical or any other type can be used as gyroscope 16. However, an MEMS sensor can suitably be used because it is compact and is easily incorporated into body 1. A rate integrating gyro or an orientation gyro that outputs an angle may be used in place of a rate gyro that outputs an angular velocity. Furthermore, output of the gyroscope may be bandpass filtered in order to remove noise (for example, a frequency component of around 100 Hz to 300 Hz which is the driving frequency of the brush) resulting from vibration of the brush.

When toothbrush body 1 is in a still state (for example, the brush is continuously applied to one section being brushed), substantially only a gravitational acceleration component is included in output of acceleration sensor 15. In this case, the three-dimensional orientation of the brush can be detected accurately, so that the section being brushed and the brush angle can be estimated with high precision. However, when toothbrush body 1 is in a moving state (for example, when the brush moves from one section being brushed to another section being brushed), not only a gravitational acceleration component but also a dynamic acceleration component may be included in output of acceleration sensor 15. The dynamic acceleration component is an unnecessary signal component (noise) in calculation of the three-dimensional orientation. On the other hand, output of gyroscope 16 is not observed when toothbrush body 1 is in a still state, and a significant signal is output only when toothbrush body 1 is moving. Using such a difference in sensor characteristics, in the present embodiment, the three-dimensional orientation of the toothbrush is detected based on outputs of both of acceleration sensor 15 and gyroscope 16.

Specifically, in the orientation detection process (S10 in FIG. 5), CPU 120 first obtains output of acceleration sensor 15 and output of gyroscope 16. When the absolute value of output of gyroscope 16 is smaller than a predetermined threshold value, CPU 120 regards toothbrush body 1 as being still and finds the three-dimensional orientation from the outputs Ax, Ay, Az of acceleration sensor 15. When the absolute value of output of gyroscope 16 in any one of the axes is equal to or greater than the predetermined threshold value, CPU 120 estimates the dynamic acceleration component in each direction x, y, z from output of gyroscope 16 and corrects the values of Ax, Ay, Az. Accordingly, the dynamic acceleration components included in Ax, Ay, Az are cancelled so that the three-dimensional orientation of the brush can be calculated with high precision.

It is noted that the process may be such that brush orientation detection is not performed when output of the gyroscope is obtained, rather than correcting output of the acceleration sensor using output of the gyroscope. In other words, the processes such as orientation detection, section being brushed estimation, brush angle estimation, and operation mode switching are performed only when output of the gyroscope is smaller than a predetermined threshold value. Accordingly, operation mode switching is executed only when the orientation estimated from output of the acceleration sensor has some degree of reliability.

Furthermore, the current orientation vector A=(Ax, Ay, Az) may be calculated by calculating the amount of angular change $\Delta\theta yz$ around the x-axis, the amount of angular change $\Delta\theta zx$ around the y-axis, and the amount of angular change $\Delta\theta xy$ around the z-axis from output of the gyroscope and by rotating the orientation vector A'=(Ax', Ay', Az') obtained in the orientation detection process one clock earlier by the angle ($\Delta\theta yz$, $\Delta\theta zx$, $\Delta\theta xy$). Alternatively, the orientation of the electric toothbrush may be calculated and evaluated from the angle information (see FIG. 28) of the roll angle $\alpha$, the pitch angle $\beta$, and the yaw angle $\gamma$, in place of acceleration information Ax, Ay, Az.

According to the configuration of the present embodiment as described above, the three-dimensional orientation of the electric toothbrush can be found with higher precision by combining outputs of the acceleration sensor and the gyroscope (including selection of one of outputs of the acceleration sensor and the gyroscope according to conditions). In a case of an electric toothbrush using the Bass technique with frequent translational motions, orientation information with sufficient precision can be obtained even with a combination of the acceleration sensor and the bandpass filter. However, in a case of the rolling technique in which three-dimensional rolling of the toothbrush body occurs, an error factor is significant only with the use of acceleration information, and the accuracy of orientation detection may be decreased. In such a case, the technique in the present embodiment using angular velocity information of the gyroscope is effective.

Fifth Embodiment

Figure 20:
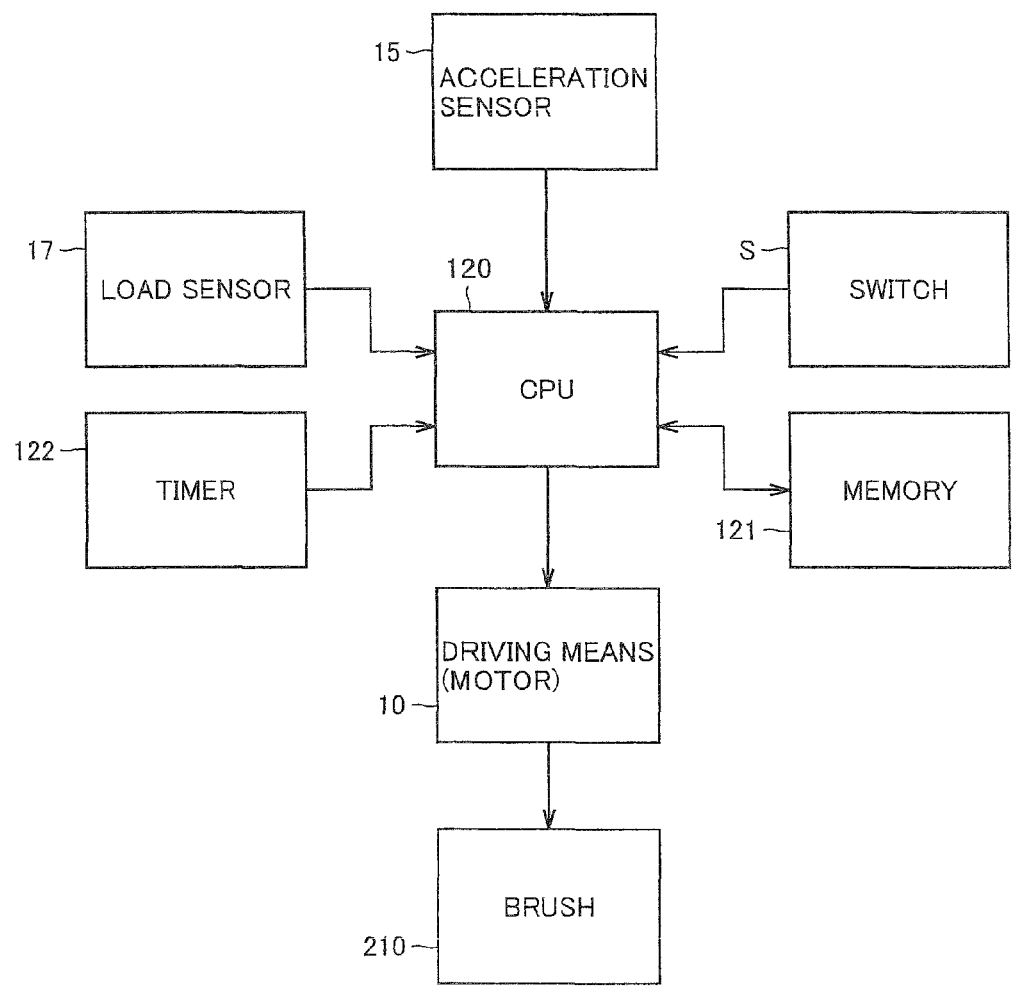
FIG. 20 is a block diagram showing an electric toothbrush in a fifth embodiment.

FIG. 20 is a block diagram of the electric toothbrush in a fifth embodiment. The electric toothbrush in the present embodiment includes a load sensor (load sensing means) 17 for sensing a load acting on the brush. A strain gauge, a load cell, a pressure sensor, or any other type can be used as load sensor 17. However, an MEMS sensor is suitably used because it is compact and is easily incorporated into body 1.

Figure 21:
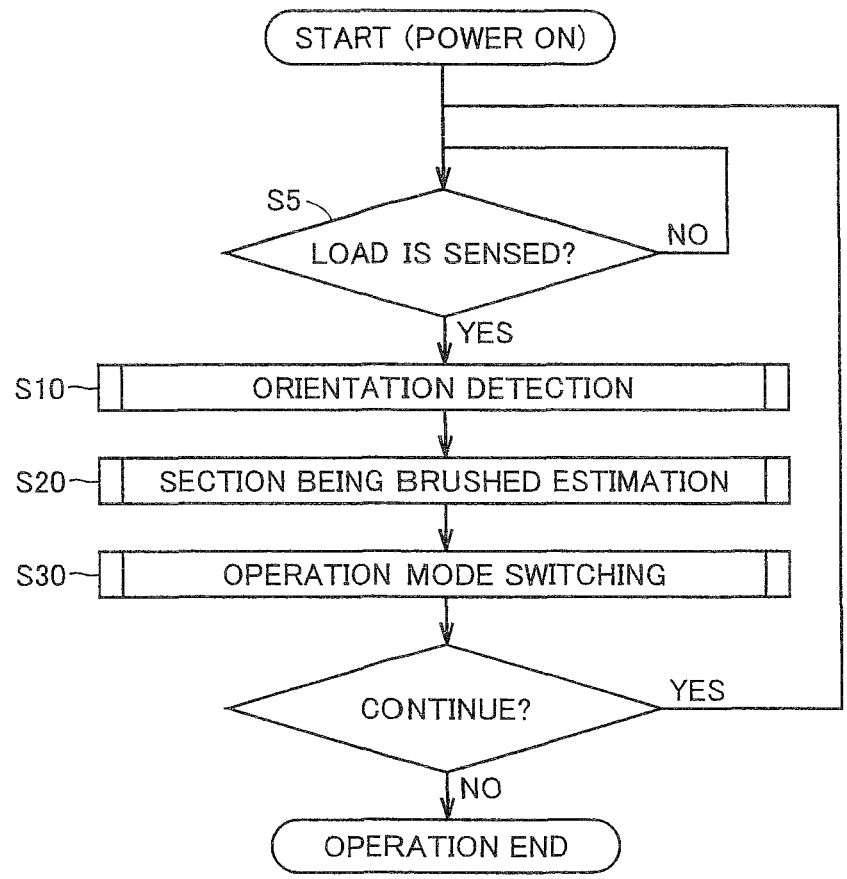
FIG. 21 is a flowchart showing a main routine of operation mode automatic control in the fifth embodiment.

FIG. 21 is a flowchart of a main routine in the fifth embodiment. It differs from the first embodiment in that a load sensing process (S5) is added.

In S5, CPU 120 determines whether a load acts on the brush or not based on load information obtained from load sensor 17. It can be regarded that "a load acts on the brush" for example when the output value of load sensor 17 exceeds a predetermined threshold value. The processes after the next step wait until a load acts on the brush (S5; NO). Accordingly, while no load is acting on the brush, the processes such as orientation detection, section being brushed estimation, brush angle estimation, and operation mode switching are prohibited.

For example, when the brush is moved from the right side to the left side of dentition, the orientation of the brush is largely changed, so that operation modes may be changed frequently during moving. Such a phenomenon is not preferable since it makes control unstable and results in wasted power consumption. Then, as in the present embodiment, by monitoring the load acting on the brush and prohibiting the processes such as orientation detection and operation mode switching as necessary, the above-noted phenomenon during moving the brush can be prevented.

It is noted that load information may be used in control of operation mode. For example, when a load acting on the brush changes, the brush vibration characteristics and resonance points change, so that first resonance and second resonance described in the third embodiment may not appear well. Then, by adjusting the frequency of the brush (the rotational speed of the motor) as appropriate according to the load acting on the brush, a shift of resonance point may be compensated for and the resonance phenomenon can be reproduced accurately. The correspondence between magnitudes of load and resonance points can be found by experiments.

Although load sensor 17 is used here, the load can be sensed by any other means. For example, as the load acting on the brush is greater, the load of the motor increases and the value of current flowing in the motor increases. Therefore, the value of current flowing in the motor is monitored, and the load acting on the brush can be estimated from the value of current.

Figure 22:
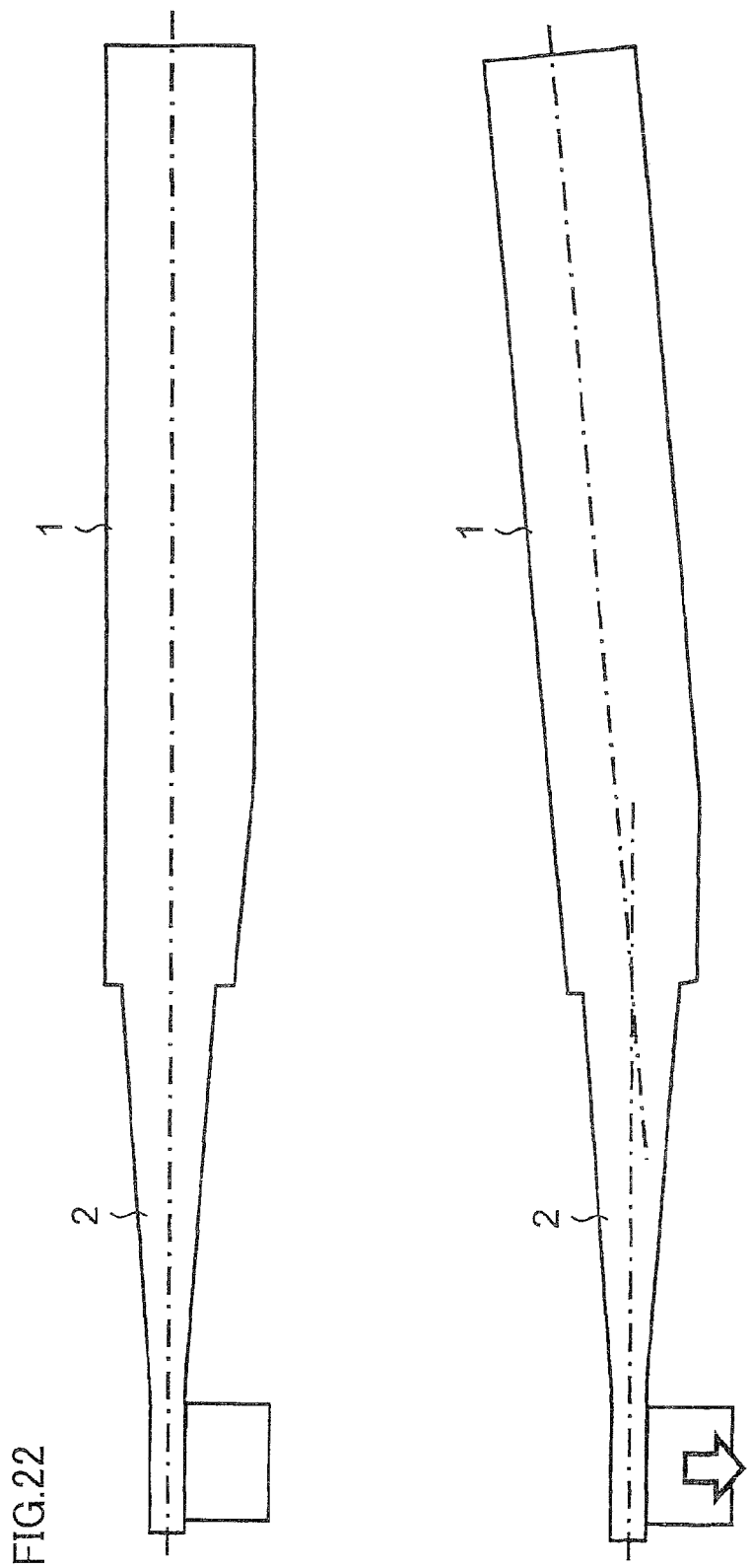
FIG. 22 is a diagram showing an orientation change of a toothbrush body when the brush is pushed against teeth.
Figure 23:
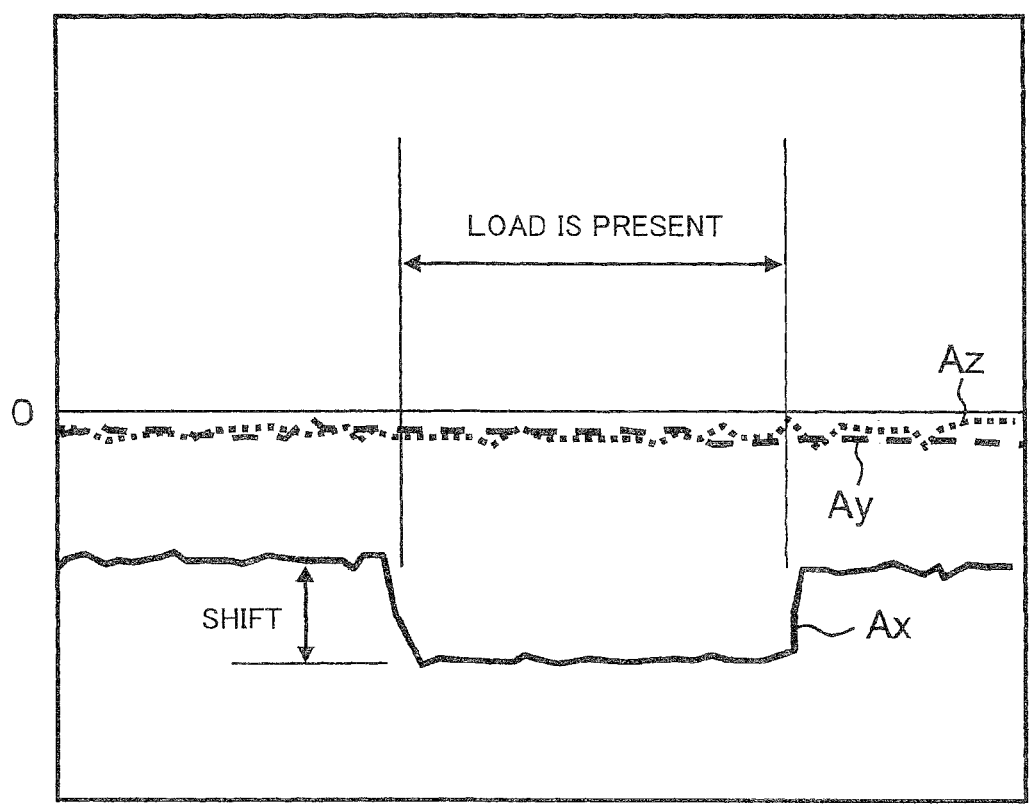
FIG. 23 is a diagram showing a waveform change of sensor output along with an orientation change in FIG. 22.

Alternatively, whether a load acts on the brush or not can also be sensed by monitoring output of acceleration sensor 15. As shown in FIG. 22, when the user grips toothbrush body 1 and pushes the bristles of the brush against the teeth, the elastic member between toothbrush body 1 and vibrating member 2 is deformed and the orientation of toothbrush body 1 slightly changes. This orientation change can be observed as a waveform change of acceleration sensor output, for example, as shown in FIG. 23. In other words, at the instant when the orientation changes, the level of at least one sensor output is slightly shifted, and the shifted level is maintained while the brush is being pushed against the teeth. Whether a load acts on the brush or not can be determined by capturing such a waveform change. Of course, this method is difficult for high-precision load estimation but is practical enough for determination at such a level as "whether a load acts or not" as in S5 in the fifth embodiment. The use of acceleration sensor 15 as a load sensing means as described above is preferable in that the number of components is reduced, and as a result, size reduction and cost reduction of the toothbrush are achieved.

Sixth Embodiment

Figure 24:
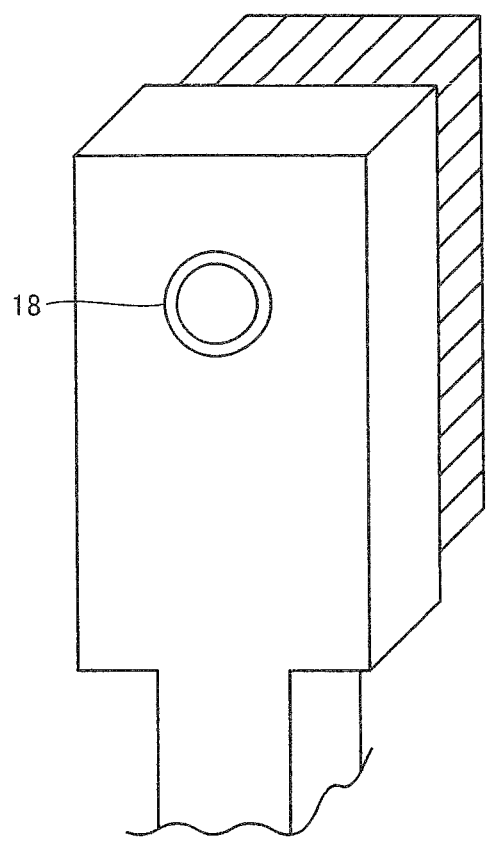
FIG. 24 is a perspective view showing a brash portion of the electric toothbrush in a sixth embodiment.

FIG. 24 shows a brush portion of the electric toothbrush in a sixth embodiment. The electric toothbrush in the present embodiment includes a temperature sensor 18 for detecting a temperature of the brush portion. Temperature sensor 18 is installed on the back face of the brush. An infrared sensor, a thermistor, or any other type may be used as temperature sensor 18.

Figure 25:
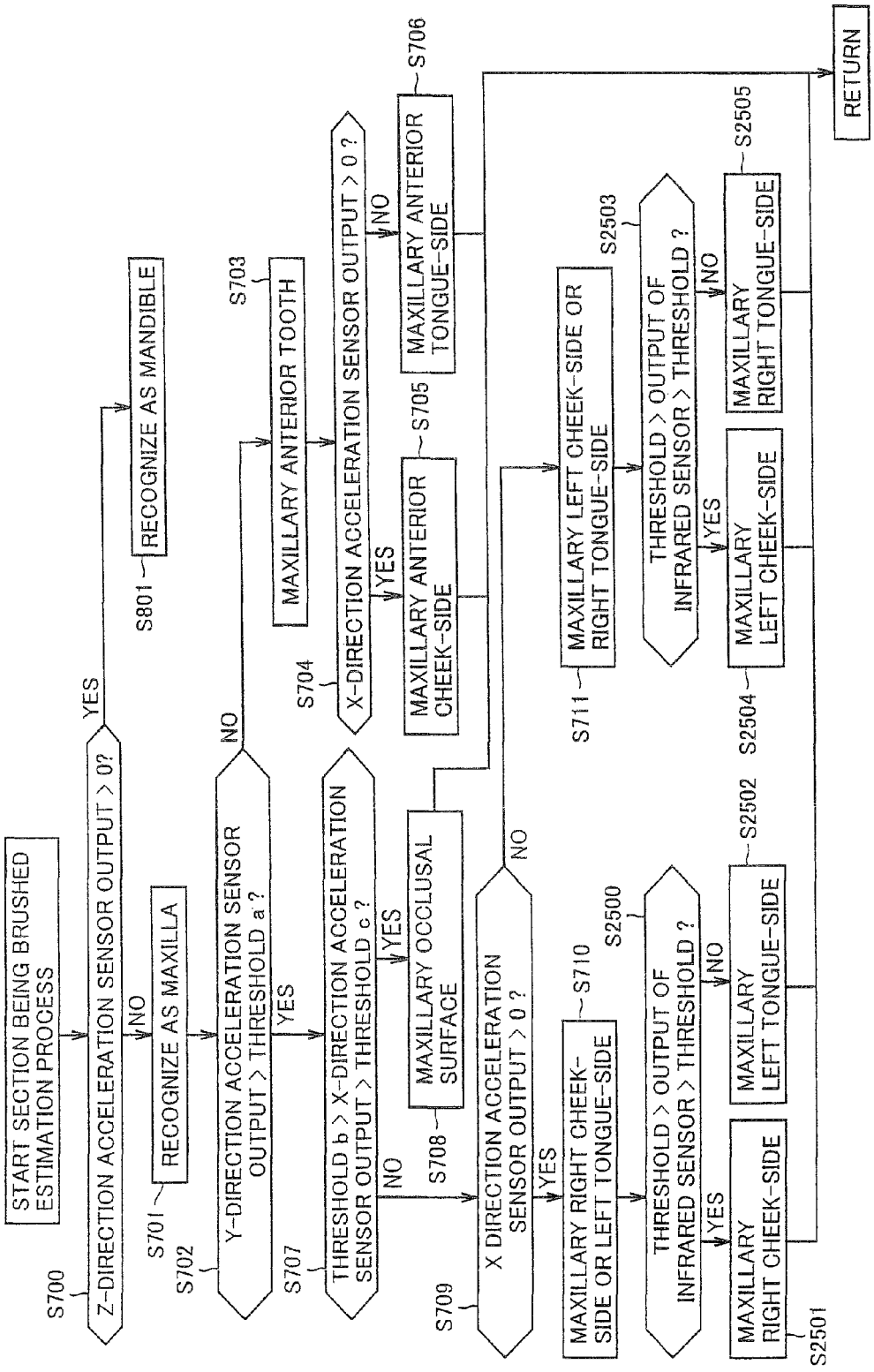
FIG. 25 is a flowchart of a section being brushed estimation process (maxilla) in the sixth embodiment.
Figure 26:
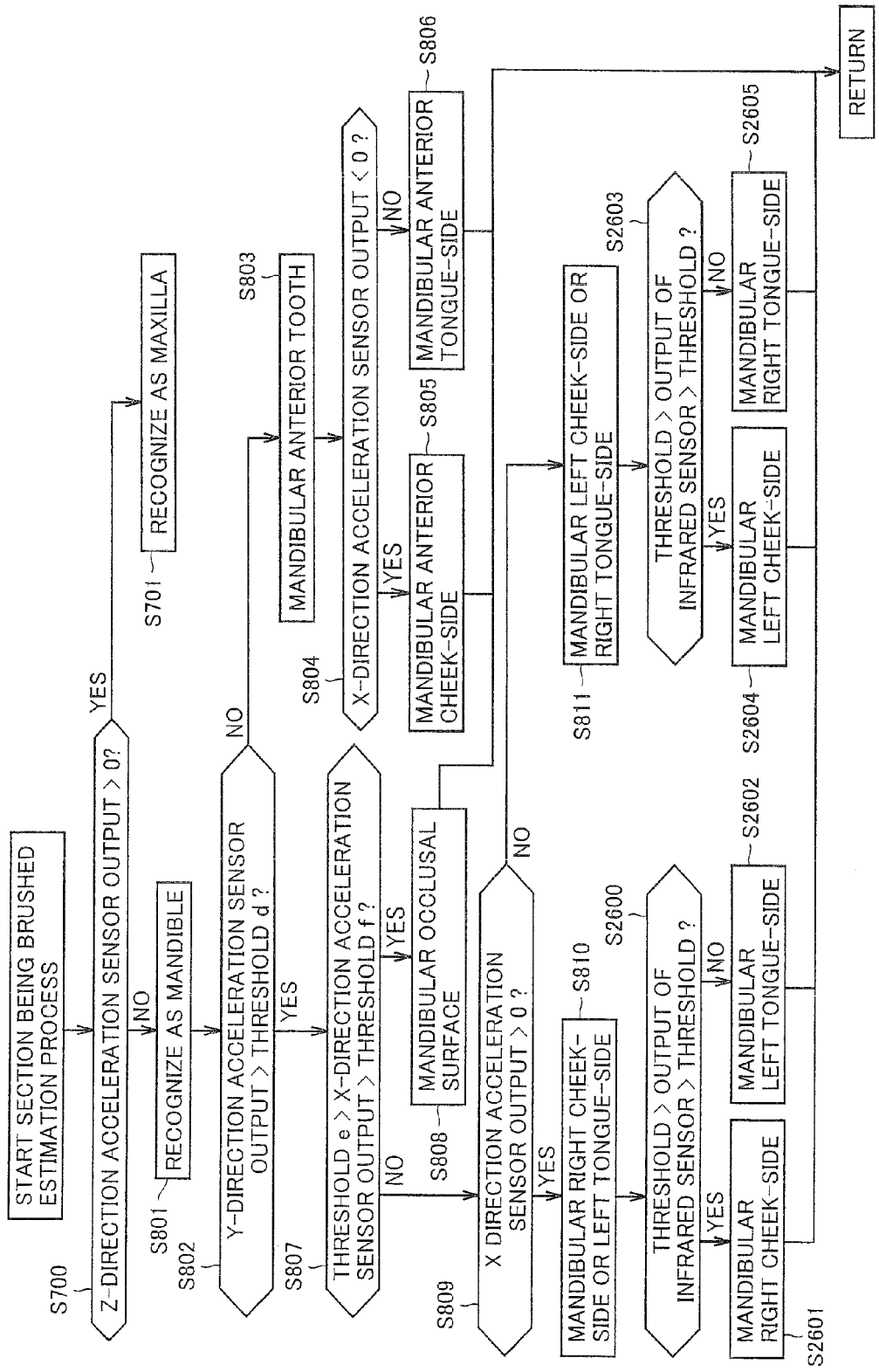
FIG. 26 is a flowchart of a section being brushed estimation process (mandible) in the sixth embodiment.

FIG. 25 and FIG. 26 are flowcharts of a section being brushed estimation process (S20). It differs from the section being brushed estimation process (FIG. 7, FIG. 8) in the first embodiment in that the cheek-side and the tongue-side are distinguished from each other based on output of temperature sensor 18.

The process for maxilla in FIG. 25 narrows down to "maxillary left cheek-side or maxillary right tongue-side" based on output of acceleration sensor 15 (S710), and then CPU 120 determines whether the output value of temperature sensor 18 falls in a predetermined range or not (S2500). If the brush is on the cheek-side, temperature sensor 18 is in contact with or in proximity to the back side of the cheek, and therefore the obtained output value is close to the temperature of the human body. By contrast, when the brush is on the tongue-side, temperature sensor 18 is exposed to the outside air, and therefore the obtained output value is lower than the temperature of the human body. Therefore, CPU 120 determines as being "maxillary right cheek-side" if the output value of temperature sensor 18 is in the range of 36 degrees to 38 degrees Celsius (S2501), and otherwise determines as being "maxillary left tongue-side" (S2502). Similarly, "maxillary left cheek-side" and "maxillary right tongue-side" can be distinguished from each other based on the output value of temperature sensor 18 (S2503-S2505). In the process for mandible, it is possible to distinguish between "mandibular left tongue-side" and "mandibular right cheek-side" (S2600-S2602) as well as between "mandibular right tongue-side" and "mandibular left cheek-side" (S2603-S2605) similarly, based on the output of temperature sensor 18.

As described above, in the present embodiment, the section being brushed can be distinguished more finely than in the first embodiment, so that more flexible operation mode control can be realized.

Seventh Embodiment

Figure 30:
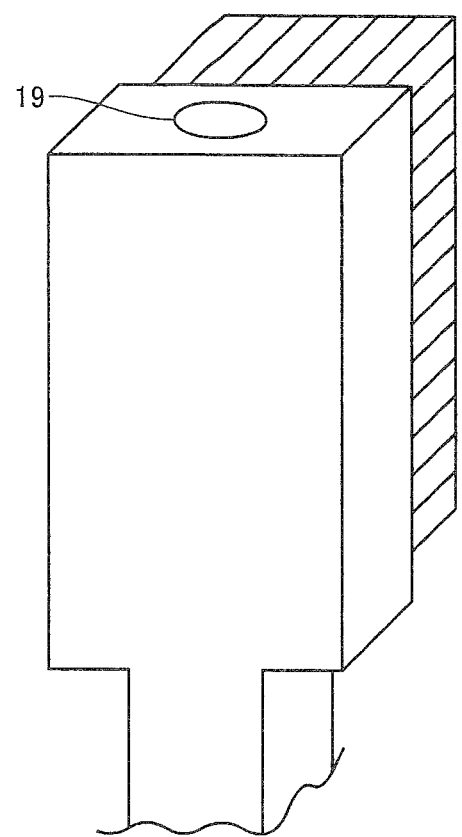
FIG. 30 is a perspective view showing a brush portion of the electric toothbrush in a seventh embodiment.

FIG. 30 is a brush portion of the electric toothbrush in a seventh embodiment. In the sixth embodiment, temperature information obtained by temperature sensor 18 is used to identify a section being brushed (distinguish between the cheek-side and the tongue-side). In the present seventh embodiment, image information is used.

As shown in FIG. 30, a camera 19 is provided at the tip end in the y-axis direction of the brush head. A visible light camera, an infrared camera, or any other camera may be used as camera 19 as long as information of images in the oral cavity can be obtained. An infrared camera is to monitor radioactive heat (also called thermography). An infrared camera is more preferable than a visible light camera because the oral cavity may be dark during brushing. In the present embodiment, the resolution of the camera may not be so high as long as the profile of uvula is known as described below.

Similarly to the sixth embodiment, CPU 120 narrows down to "maxillary left cheek-side or maxillary right tongue-side" based on output of acceleration sensor 15 (see S710 in FIG. 25). Then, CPU 120 obtains an image from camera 19 and detects the uvula from the image. Well-known image analysis techniques can be used in detection of uvula. For example, the uvula profile may be detected by edge extraction or Hough transform, or the uvula may be detected by pattern matching. When the brush is on the tongue-side, the tip end of the brush head faces toward the throat, and therefore there is a high probability that the uvula is captured in the image. On the other hand, when the brush is on the cheek-side, the uvula is not captured in the image. Therefore, CPU 120 determines as being "maxillary right tongue-side" if the uvula can be detected, and determines as being "maxillary left cheek-side" if the uvula cannot be detected. In a similar way, it is possible to distinguish between "maxillary left cheek-side" and "maxillary right tongue-side," between "mandibular left tongue-side" and "mandibular right cheek-side," and between "mandibular right tongue-side" and "mandibular left cheek-side."

As described above, in the present embodiment, the section being brushed can be distinguished more finely than in the first embodiment, so that more flexible operation mode control can be realized.

Although in the present embodiment image information is used only for distinction between the cheek-side and the tongue-side, image information may also be used for distinction between maxilla and mandible, distinction between anterior-side, right-side and left-side, and the like. Furthermore, it is also preferable that all the section being brushed are identified based on image information. However, the oral cavity is narrow and it is difficult to know the whole positional relation. Therefore, the orientation information obtained by the acceleration sensor (acceleration sensor and gyroscope) is desirably used together rather than using only image information to identify all the section being brushed. Although the uvula is detected in the present embodiment, any other parts in the oral cavity (for example, tongue, throat, teeth, gums, etc.) may be recognized in order to determine the position and orientation of the brush. For example, it can be determined that the brush is on the tongue-side if tongue or throat is captured in the image.

It is also preferable that an optical sensor is provided at the brush portion, in place of a camera. The cheek-side and the tongue-side can be distinguished from each other by analyzing output of the optical sensor, as it is entirely dark on the cheek-side while light is detected on the tongue-side.

Eighth Embodiment

An eighth embodiment employs a configuration in which orientation detection and section being brushed identification are carried out by a single-axis acceleration sensor.

The upper figure in FIG. 31 shows a state in which a tooth surface on the cheek-side or the tongue-side is brushed. Here, the brush angle (yaw angle $\gamma$) is about 90 degrees, the x-axis direction component of gravitational acceleration is about 1 g or −1 g (positive or negative corresponds to the left or right dentition), and the z-axis direction component of gravitational acceleration is almost zero. On the other hand, the lower figure in FIG. 31 shows a state in which an occlusal surface is brushed. Here, the brush angle (yaw angle $\gamma$) is almost 0 degree, the x-axis direction component of gravitational acceleration is almost zero, and the z-axis direction component of gravitational acceleration is about 1 g or −1 g (positive or negative corresponds to the upper or lower dentition).

Such characteristics can be used to distinguish between "cheek-side or tongue-side tooth surface" and "occlusal surface" and additionally distinguish between left, right, top, and bottom only with an x-axis acceleration sensor or a z-axis acceleration sensor. As for the operation mode control, for example, the driving speed of the brush may be decreased so as not to stimulate gums in brushing "cheek-side or tongue-side tooth surface" while the driving speed of the brush may be increased in brushing "occlusal surface".

Ninth Embodiment

A ninth embodiment is a technique of estimating a section being brushed and a brush angle that are orientation information by complementing output of the acceleration sensor and output of the gyroscope with each other. In the present embodiment, the section being brushed and the brush angle at a point of time $t=n(n>0)$ are calculated by first finding the orientation information (the section being brushed and the brush angle at a point of time $t=0$) at a reference position (also called an initial position) of the toothbrush, thereafter taking in outputs of the acceleration sensor and the gyroscope every one clock, and then accumulatively adding the amounts of relative movement and the amounts of relative rotation with respect to outputs one clock earlier.

The orientation at a time of power-on on may be set as a reference position. Alternatively, such a mechanism may be provided that allows the user to input a reference position (position at the start of brushing) (for example, to press a switch in a state in which the user places the brush on the maxillary anterior cheek-side while holding the brush body in a horizontal position).

Figure 32:
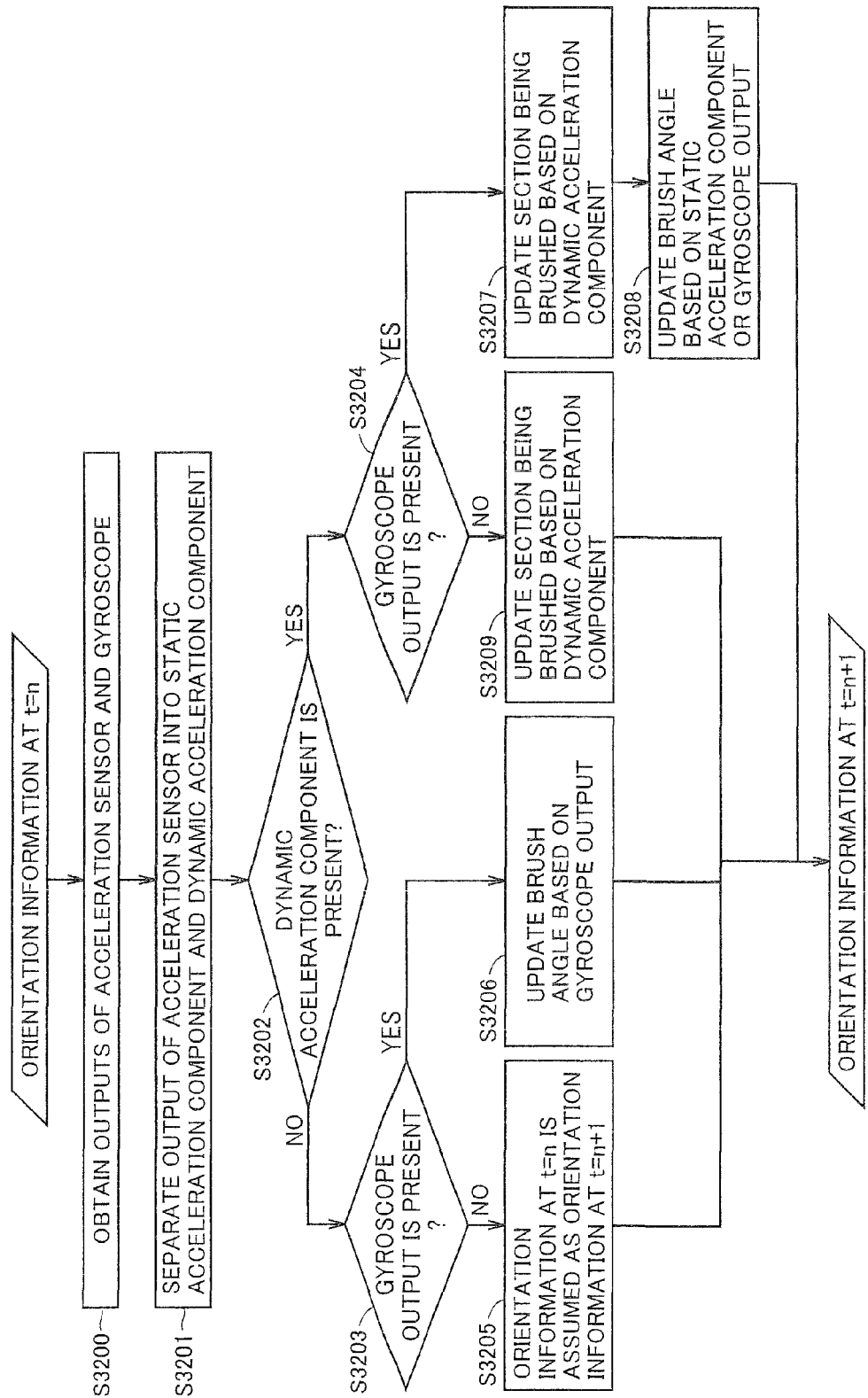
FIG. 32 is a flowchart of an orientation information updating process in a ninth embodiment.

FIG. 32 is a flowchart of an orientation information updating process in the ninth embodiment. This flowchart shows a process of calculating orientation information at $t=n+1$ from the orientation information (section being brushed and brush angle) at $t=n$ and outputs of the acceleration sensor and the gyroscope. In the following, the processing by CPU will be described according to the flowchart.

CPU first obtains outputs of the acceleration sensor and the gyroscope (S3200) and separates the output of the acceleration sensor into a static acceleration component and a dynamic acceleration component using a bandpass filter (S3201). Then, the processes differ according to the presence/absence of dynamic acceleration component (S3202) and the presence/absence of gyroscope output (S3203, S3204) as described below. It is noted that "the presence of dynamic acceleration component" means that the absolute value of dynamic acceleration component is greater than a predetermined threshold value. Similarly, "the presence of gyroscope output" means that the absolute value of output of the gyroscope is greater than a predetermined threshold value.

(1) In the Case of Absence of Dynamic Acceleration Component and Absence of Gyroscope Output In this case, there is no change in position and angle of the toothbrush, and CPU therefore outputs the orientation information at $t=n$ as the orientation information at $t=n+1$ (S3205). It is noted that the section being brushed and the brush angle at $t=n+1$ may be calculated by finding the three-dimensional orientation of the toothbrush from the static acceleration component of the acceleration sensor, rather than outputting the orientation information at $t=n$ as it is.

(2) In the Case of Absence of Dynamic Acceleration Component and Presence of Gyroscope Output If the toothbrush body is rotated around the axis in the gravitational acceleration direction in a state in which any one axis of the acceleration sensor coincides with the direction of the gravitational acceleration, output of the acceleration sensor does not change at all (only the static acceleration component is observed). Therefore, when the orientation information is calculated only from output of the acceleration sensor, the rotational motion around the axis cannot be detected and an error may be caused. Such a phenomenon may occur in a situation in which the toothbrush body is likely to fall in a vertical orientation (that is, the orientation in which the y-axis coincides with the direction of gravitational acceleration), for example, during brushing in bending posture.

Then, when there is no change in output of the acceleration sensor and there is a change in output of the gyroscope, CPU updates the orientation information using only output of the gyroscope. Here, a significant change of output of the gyroscope appears only in the rotation around the axis that coincides with the direction of gravitational acceleration. In the present embodiment, only the rotation around the y-axis is considered since rotational motion around the x-axis and rotational motion around the z-axis hardly occur in the actual brushing operation. The rotational motion around the y-axis mainly causes a change in brush angle, and CPU therefore finds the brush angle at a time of t=n+1 by calculating angular change amount $\Delta\theta zx$ around the y-axis from output of the gyroscope and adding $\Delta\theta zx$ to the brush angle at a time of t=n (S3206).

In this manner, by making use of information of the gyroscope, a brush angle change caused by rotational motion around the axis that cannot be detected only by the acceleration sensor can be calculated accurately.

It is noted that it is also possible to consider not only a rotational motion around the y-axis but also a rotational motion around the x-axis or the z-axis. For example, a rotational motion around the x-axis mainly causes the brush position to shift. Then, the brush position at a time of t=n+1 can be found by calculating the amount of movement of the brush itself from the amount of angular change around the x-axis and the distance from the rotation center to the brush and then adding the calculated amount to the brush position at a time of t=n.

(3) In the Case of Presence of Dynamic Acceleration Component and Presence of Gyroscope Output In this case, CPU finds the section being brushed at a time of t=n+1 using the respective dynamic acceleration components in the x-axis direction, the y-axis direction, and the z-axis direction obtained from acceleration sensor output (S3207). Specifically, CPU finds the brush position at a time of t=n+1 by calculating the respective amounts of movement in the x-axis direction, the y-axis direction, and the z-axis direction per clock from double integrals of dynamic acceleration components and then adding the calculated amounts of movement to the brush position at a time of t=n. The finding of the brush position (the relative position with respect to the reference position) allows estimation of the section being brushed. Furthermore, it is also preferable to estimate the section being brushed from the static acceleration component of the acceleration sensor and compare the estimation result from the static acceleration component with the estimation result from the dynamic acceleration component thereby to improve estimation precision.

In addition, information of the movement amount and the movement direction can be used to narrow down the section being brushed. For example, first, similarly to the section being brushed estimation process in the first embodiment (see FIG. 7 and FIG. 8), CPU uses the static acceleration component of the acceleration sensor to specify the section being brushed as any one of "maxillary anterior cheek-side," "maxillary anterior tongue-side," "maxillary occlusal surface," "maxillary right cheek-side or maxillary left tongue-side," "maxillary left cheek-side or maxillary right tongue-side," "mandibular anterior cheek-side," "mandibular anterior tongue-side," "mandibular occlusal surface," "mandibular right cheek-side or mandibular left tongue-side," and "mandibular left cheek-side or mandibular right tongue-side." At this stage, it is difficult to distinguish between "maxillary right cheek-side" and "maxillary left tongue-side." Similarly, it is also difficult to distinguish between "maxillary left cheek-side" and "maxillary right tongue-side," between "mandibular right cheek-side" and "mandibular left tongue-side," and between "mandibular left cheek-side" and "mandibular right tongue-side." Then, CPU evaluates the amount of movement of the brush by comparing the amount of movement of the brush (moving distance) per unit time calculated from the dynamic acceleration component with a predetermined threshold value. If the amount of movement exceeds the threshold value, CPU determines that there is a change in section being brushed between before and after movement, and otherwise determines there is no change in section being brushed. Then, if it is determined that there is a change in section being brushed, CPU narrows down the section being brushed based on the section being brushed before movement (at a time of t=n) and the amount of movement and the moving direction this time. For example, if the section being brushed at a time of t=n is the right-side dentition and the moving direction is leftward, the section being brushed after movement can be specified as the left-side dentition. This information allows to make a distinction, for example, between "maxillary right cheek-side" and "maxillary left tongue-side" thereby to narrow down the section being brushed in more details.

Furthermore, the brush angle can be calculated in the following two ways: the angle is calculated from the static acceleration component of the acceleration sensor; and the angle is calculated by adding the amount of angular change around the y-axis obtained from output of the gyroscope to the brush angle one clock earlier. The former technique is advantageous in that the absolute angle of the brush can be calculated. However, according to studies by the present inventors, it is disadvantageous in that a brush angle calculation error increases as the inclination of the toothbrush body increases, although a brush angle calculation error is little when the toothbrush body assumes a horizontal orientation. On the other hand, the latter technique is advantageous in that the amount of angular change around the y-axis can be calculated directly but it is disadvantageous in that an accumulative error occurs since only a relative angle is calculated.

Then, it is preferable to switch between the former technique and the latter technique depending on the orientation of the toothbrush body. Specifically, the horizontality of the toothbrush body is evaluated using the absolute value $|y|$ of the static acceleration component of the acceleration sensor in the y direction. As $|y|$ approaches 0 G, the toothbrush body is regarded as being horizontal. CPU monitors the value of $|y|$ for each clock and outputs the brush angle calculated based on output of the gyroscope $|y|$ is equal to or greater than a predetermined threshold value (that is, if horizontality is small) (S3208). For example, if the reference angle (equal to the brush angle one clock earlier) of the gyroscope is 45 degrees and the amount of angular change around the y-axis that is calculated from output of the gyroscope at the present clock is −15 degrees, the brush angle is calculated as 30 degrees. On the other hand, if $|y|$ is smaller than the threshold value (that is, if horizontality is large), the brush angle is calculated based on output of the acceleration sensor (S3208). If horizontality of the toothbrush body is high, the absolute values of static acceleration components of the acceleration sensor in the x direction and the acceleration sensor in the z direction are generally as follows:

brush angle≈0 degree: $|x|≈0$, $|z|≈1$ brush angle≈45 degrees: $|x|≈|z|≈0.707$ brush angle≈90 degrees: $|x|≈1$, $|z|≈0$.

Therefore, the brush angle can be calculated by evaluating $|x|$ or $|z|$ or both. Here, if the brush angle is calculated as 30 degrees from output of the acceleration sensor, the reference angle of the gyroscope is calibrated to 30 degrees using that value. Accordingly, an error caused by accumulative addition can be reduced as soon as possible. Although the horizontality of the toothbrush body is evaluated using the value of $|y|$ here, it is also preferable to evaluate the horizontality of the toothbrush body, taking the values of $|x|$ and $|z|$ into consideration.

(4) In the Case of Presence of Dynamic Acceleration Component and Absence of Gyroscope Output This corresponds to the case where the toothbrush body makes straight-ahead (translational) motion. However, the state of (4) rarely takes place in the operation during brushing since the oral cavity is narrow. It is noted that also in the case of (4), similarly to the case of (3), the section being brushed can be calculated from the dynamic acceleration component (S3209).

According to the technique in the present embodiment as described above, the section being brushed and the brush angle can be calculated accurately by complementing output of the acceleration sensor and output of the gyroscope with each other.

(Others)

The configurations of the foregoing embodiments are only illustrated as examples of the present invention. The scope of the present invention is not limited to the foregoing embodiments and various modifications can be made within the scope of the technical idea thereof. For example, it is preferable that the configurations of the foregoing embodiments may be combined with each other. Although a vibratory electric toothbrush using eccentric weight has been illustrated in the foregoing embodiments, the present invention is also applicable to an electric toothbrush employing any other motion. For example, the present invention is also applicable to an electric toothbrush employing rotational reciprocating motion, linear reciprocating motion, brush bristles rolling motion, or a combination of these motions in a switchable manner. In this case, operation mode can be switched by switching a motion frequency depending on a section being brushed or by switching between rotational reciprocating motion and linear reciprocating motion. Furthermore, the present invention is preferably applicable to an electric toothbrush of a type which has an ultrasonic vibrating element at the brush portion and performs brushing using both brush vibration and ultrasonic wave.

Furthermore, it is also preferable that the position of the brush is calculated using orientation information obtained from a magnetic sensor or the like. A bandpass filter such as a hypass filter can be used to extract a dynamic acceleration component from acceleration sensor output. Here, in order to remove noise caused by vibration of the brush, it is also preferable to cut a frequency component of 100 Hz to 300 Hz that corresponds to the driving frequency of the brush. As for anterior teeth, the orientation of the brush changes 180 degrees depending on whether the user holds the toothbrush body by the left hand or the right hand. Therefore, the user may be allowed to register the dominant hand (the hand by which the user holds a toothbrush) so that an algorithm for determining a section being brushed or an operation mode (motor rotational direction, movement of the brush) is changed according to the registered dominant hand.

The toothbrush body may be provided with a concave/convex shape for guiding (or defining) a grip position. For example, if projections and depressions are present at a tip end portion of the toothbrush body (the position that is touched by the tip or joint of the thumb or index finger when the user grips the toothbrush body), the user consciously or unconsciously holds the toothbrush in such a manner as to fit the fingers on the projections and depressions. This is used to introduce the user into a predetermined grip state. Typically, if the orientation of the brush in the angle around the y-axis (the negative direction in the z-axis) in FIG. 3 is 0 degree, two projections (or depressions) are provided at positions of about ±45 degrees and two depressions (or projections) are provided at positions of about ±135 degrees. When the user grips the toothbrush with his/her fingers resting on those projections and depressions, the user can easily keep the brush angle at 45 degrees.

Although in the foregoing embodiments a temperature sensor, a camera, and an optical sensor are used to identify a section being brushed (distinguish between the cheek-side and the tongue-side) by way of illustration, a distance sensor such as an ultrasonic sensor may additionally be used. For example, similarly to the temperature sensor in FIG. 24, a distance sensor is installed on the back face of the brush. When the cheek-side is brushed, the distance sensor is in proximity or in contact with the cheek and thus the measurement value of the distance sensor is extremely small. On the other hand, when the tongue-side is brushed, the distance sensor faces into the oral cavity and therefore the measurement value of the distance is relatively large. Therefore, it is possible to distinguish between the cheek-side and the tongue-side by comparing the measurement value of the distance sensor with a threshold value (for example, 5 mm).

DESCRIPTION OF THE REFERENCE SIGNS 1 electric toothbrush body
2 vibrating member
10 motor
11 rotation shaft
12 driving circuit
13 rechargeable battery
14 coil
15 acceleration sensor
16 gyroscope
17 load sensor
18 temperature sensor
19 camera
20 stem portion
21 brush part
30 eccentric shaft
100 charger
120 CPU
121 memory
122 timer
202 elastic member
203 bearing
210 brush
300 weight
S switch

The invention claimed is:

1. An electric toothbrush comprising:
a brush;
a motor having a rotational shaft;
an eccentric shaft having a first end and a second end, the first end being fixed to the rotation shaft of the motor and the second end being connected to the brush, wherein said brush vibrates in accordance with a rotational speed of the motor;
an orientation detector configured to detect an orientation of said brush;
a section estimation device configured to estimate a section being brushed based on the detected orientation; and
a controller configured to control the rotational speed of the motor such that a vibration frequency of the brush is changed based on a change of the estimated section being brushed, wherein said orientation detector includes an acceleration sensor configured to detect a three-dimensional orientation of said brush based on output of said acceleration sensor.

2. The electric toothbrush according to claim 1, wherein said orientation detector includes an acceleration sensor and a gyroscope, the orientation detector being configured to detect a three-dimensional orientation of said brush based on an output of said acceleration sensor and an output of said gyroscope.

3. The electric toothbrush according to claim 1, further comprising:
a brush angle estimation device configured to estimate a brush angle that is an angle of said brush with respect to a tooth axis, based on the detected orientation,
wherein said controller controls the rotational speed based on the estimated section being brushed and the estimated brush angle.

4. The electric toothbrush according to claim 1, further comprising:
a load sensor configured to sense a load acting on said brush,
wherein said controller prohibits the change of the rotational speed while no load is acting on said brush.

5. An electric toothbrush comprising:
a brush;
a motor having a rotational shaft;
an eccentric shaft having a first end and a second end, the first end being fixed to the rotation shaft of the motor and the second end being connected to the brush, wherein said brush vibrates in accordance with a rotational speed of the motor;
an orientation detector configured to detect an orientation of said brush;
a section estimation device configured to estimate a section being brushed based on the detected orientation; and
a controller configured to control the rotational speed of the motor such that a vibration frequency of the brush is changed based on a change of the estimated section being brushed, wherein said orientation detector detects each of 45 degrees and 90 degrees as an orientation of the brush.

6. An electric toothbrush comprising:
a brush;
a motor having a rotational shaft;
an eccentric shaft having a first end and a second end, the first end being fixed to the rotation shaft of the motor and the second end being connected to the brush, wherein said brush vibrates in accordance with a rotational speed of the motor;
an orientation detector configured to detect an orientation of said brush;
a section estimation device configured to estimate a section of teeth, out of a plurality of sections of teeth, being brushed based on the detected orientation; and
a controller configured to control the rotational speed of the motor such that a vibration frequency of the brush is changed based on a change of the estimated section being brushed.

* * * * *